(12) United States Patent
Patel et al.

(10) Patent No.: US 10,188,377 B2
(45) Date of Patent: Jan. 29, 2019

(54) SEMI-AUTOMATIC SUTURING MACHINE

(71) Applicants: Ruchi Patel, Princeton Junction, NJ (US); Giovanni Sanchez, Jericho, NY (US)

(72) Inventors: Ruchi Patel, Princeton Junction, NJ (US); Giovanni Sanchez, Jericho, NY (US)

(73) Assignee: Ruchi Patel, Princeton Junction, NJ (US)

( * ) Notice: Subject to any disclaimer, the term of this patent is extended or adjusted under 35 U.S.C. 154(b) by 0 days.

(21) Appl. No.: 15/215,573

(22) Filed: Jul. 20, 2016

(65) Prior Publication Data
US 2018/0000475 A1    Jan. 4, 2018

Related U.S. Application Data

(60) Provisional application No. 62/195,226, filed on Jul. 21, 2015.

(51) Int. Cl.
| | |
|---|---|
| *A61B 17/00* | (2006.01) |
| *A61B 17/04* | (2006.01) |
| *A61B 17/08* | (2006.01) |
| *A61B 17/062* | (2006.01) |

(52) U.S. Cl.
CPC .......... *A61B 17/04* (2013.01); *A61B 17/0482* (2013.01); *A61B 17/0487* (2013.01); *A61B 17/0491* (2013.01); *A61B 17/062* (2013.01); *A61B 2017/0023* (2013.01); *A61B 2017/0053* (2013.01); *A61B 2017/00349* (2013.01); *A61B 2017/0472* (2013.01); *A61B 2017/0488* (2013.01); *A61B 2017/081* (2013.01)

(58) Field of Classification Search
CPC ............ A61B 17/0491; A61B 17/0487; A61B 2017/0488; A61B 17/0483; A61B 17/04; A61B 17/0482; A61B 17/062; A61B 2017/0023; A61B 2017/00349; A61B 2017/0053; A61B 2017/0472; A61B 2017/081
See application file for complete search history.

(56) References Cited

U.S. PATENT DOCUMENTS

| | | |
|---|---|---|
| 2,327,353 A | 8/1943 | Karle |
| 2,577,240 A | 12/1951 | Findley |
| 2,580,964 A | 1/1952 | Skaller |
| 3,082,426 A | 3/1963 | Miles |
| 3,807,407 A | 4/1974 | Schweizer |

(Continued)

*Primary Examiner* — Kortney L. Klinkel

(57) ABSTRACT

The present invention contemplates a hand-held and hand-operable stitching device capable of securely placing a single interrupted suture through a wound using sterile suturing material with a single squeeze of the device's arms. Operating substantially faster than a surgeon, the compact and lightweight device employs an intuitive stapler-like structure and a center assembly capable of closing a wound with traditional suturing material secured by anchors that remain on either side of the wound. The apparatus employs needle-suture units stored in a center assembly and deployed individually when the device is actuated. When actuated, an epicyclic gear train within a center assembly causes a needle-suture unit to rotate through a circular path through the tissue, bringing the edges of separated tissue together. The suture thread is then secured in its position with anchors and the needle is then disjointed from the suture thread with a blade.

2 Claims, 44 Drawing Sheets

(56) References Cited

U.S. PATENT DOCUMENTS

| | | |
|---|---|---|
| 4,236,470 A | 12/1980 | Stenson |
| 4,506,669 A | 3/1985 | Blake, III |
| 4,508,253 A | 4/1985 | Green |
| 4,557,265 A | 12/1985 | Andersson |
| 5,477,794 A | 12/1995 | Klundt |
| 6,346,111 B1 | 2/2002 | Gordon |
| 7,004,950 B1 | 2/2006 | Collins |
| 7,833,235 B2 | 11/2010 | Chu |
| 8,551,122 B2 | 10/2013 | Lau |

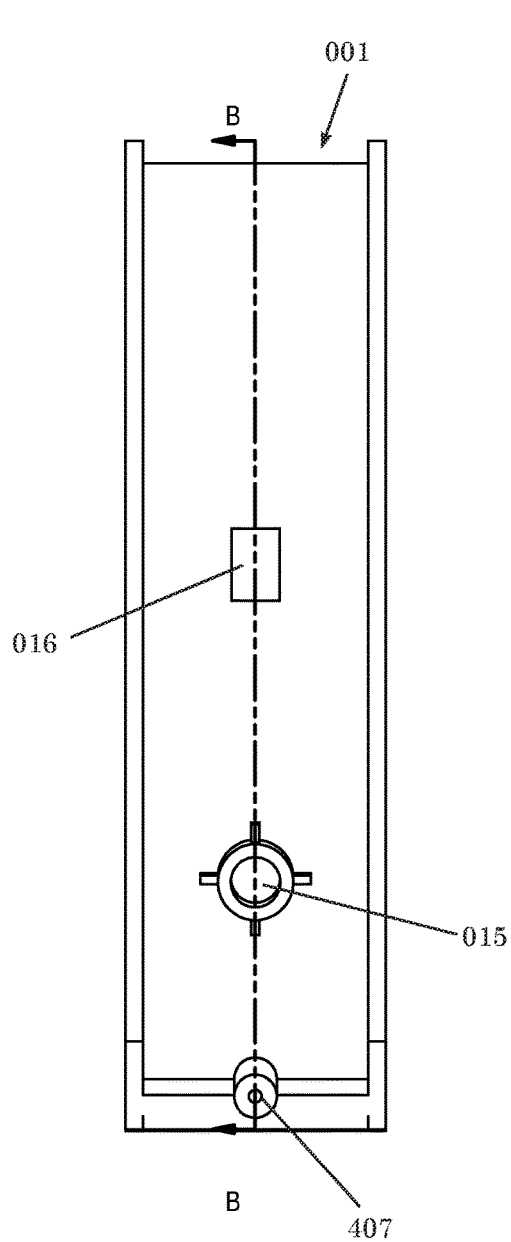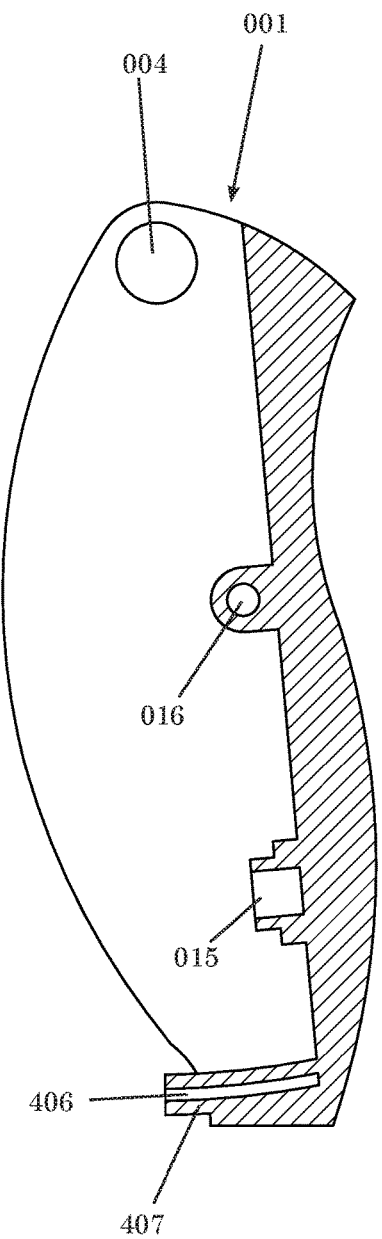
FIG. 5
FIG. 6

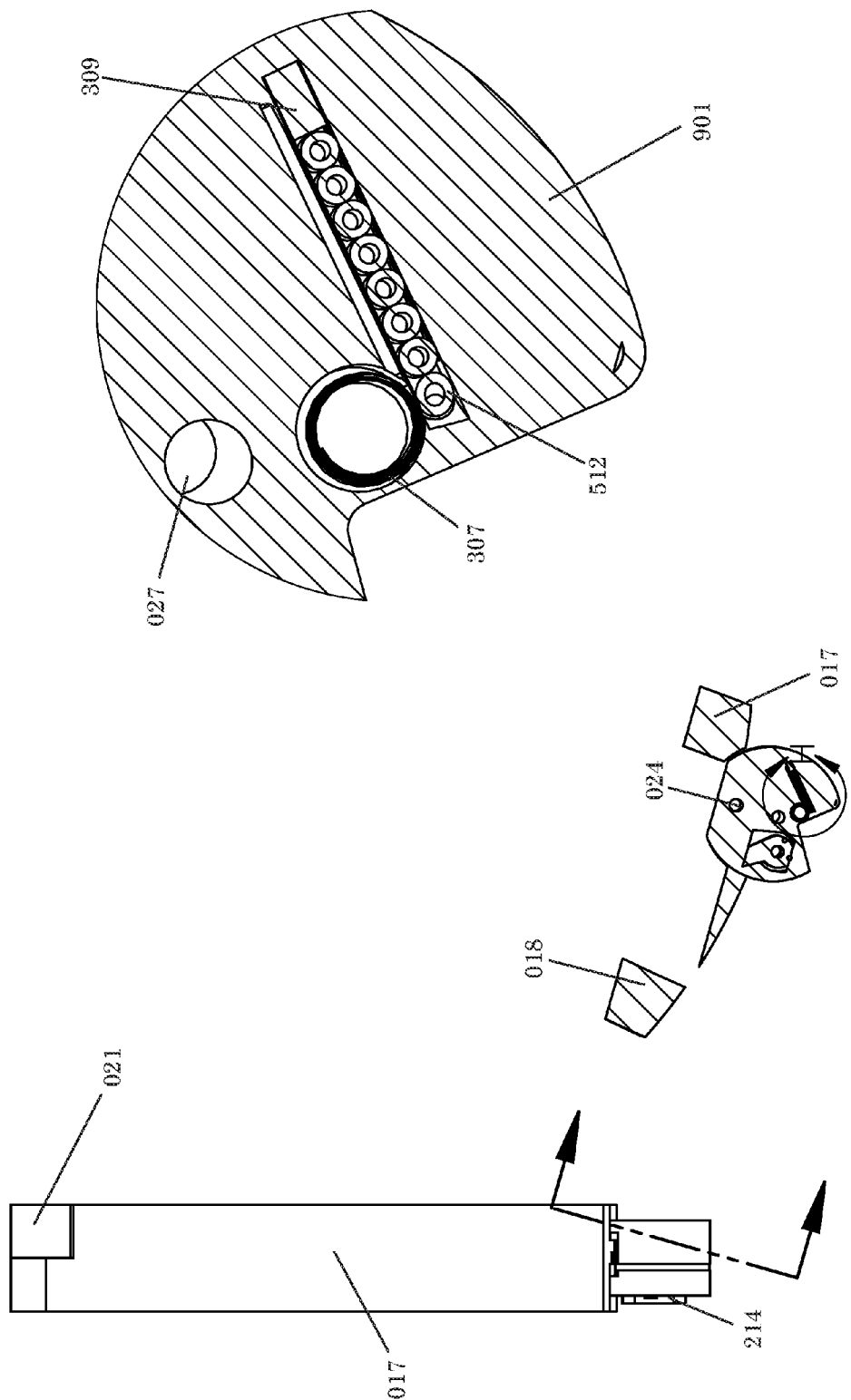

SEMI-AUTOMATIC SUTURING MACHINE

RELATED APPLICATIONS

Provisional application 62/195,226, filed on Jul. 21, 2015.

FIELD OF THE INVENTION

This invention relates to a device, apparatus, and method for surgical application of sutures for wound closure. The suturing device described in the present application is a mechanical hand-operable suture applicator to eliminate the time-consuming practice of tying knots and to reduce the risk of accidental needle-stick injury.

BACKGROUND OF THE INVENTION

Traditional manual suturing methods are slow; each hand-made stitch takes about 30-45 seconds. To enhance speed of wound closure, surgeons opt for staplers, which require about 3-5 seconds per stitch. Of all competing wound closure products, the most relevant competitor to the traditional needle and suture is the conventional surgical metal skin stapler, since seals, glues, and adhesive bandages are not suitable for deep, bloody wounds.

Although 6-15 times faster than traditional suturing, metal staples increase risk of infection by a factor of 4, requiring more most-operative visits and increased costs due to wound complications. Skin staples also leave unsightly railroad scarring due to the thickness and rigidity of stainless steel staples. Surgical stapling ultimately presents a 14 times greater risk of wound morbidity at discharge compared to suture closure. The only advantage of stapling is speed of wound closure.

The present invention aims to satisfy the need for rapid wound closure by matching the speed of the surgical stapler at 3-5 seconds per stitch. Furthermore, by utilizing traditional suturing needles and thread, the present invention aims to eliminate the risk of wound morbidity presented by metal staples.

A number of methods/products for wound closure that do not employ sutures include skin staplers, butterfly bandages, etc. These products are not relevant to our suturing device because they do not employ sutures, often the best way of closing large lacerations.

In U.S. Pat. Nos. 4,236,470 and 8,551,122, Stenson and Lau respectively teach a device that transfers a thread-holding needle between two prongs connected by a hinge in order to pass a thread from one side of a wound to another, forming a continuous suture. Stenson's device acts as a longer hand to be used in internal endoscopic procedures where the human hand cannot reach to manually make sutures. Stenson and Lau's inventions pierce the skin with a needle and drags suture material through the skin but do not make a complete suture as they do not attempt to tie off the thread. In fact, Stenson and Lau's inventions require more time than hand-made sutures and fail to complete the suturing process.

In essence, the prior art that intends to close wounds through sutures lacks either safety considerations for the user, features that allow use by those unskilled in the art of suturing, mechanisms to secure the suture, which is by far the most time-consuming component, and a mechanism that brings the edges of the wound together without the use of an additional device.

The current invention does not resemble other prior art that are considered "automatic" suturing devices because the current invention does not transfer a needle from one arm to another. Furthermore, the present invention may operate by first bringing the edges of the wound together using blunt-ended tissue prongs, eliminating the need for additional devices to assist in suturing and allow for suturing with one hand. The present invention automates the manual suturing process by pushing a needle and attached suturing material through the tissue, and securing the suture with an anchor located on the other arm of the device while reverting the arms back to their initial positions to reset the device in preparation for the next single interrupted suture.

SUMMARY OF INVENTION

It is the object of the present invention to provide the unmet need for a self-loading suturing device that is intuitively operable by those with no prior medical experience while providing improved safety of operation that prevents needle-stick injury.

The invention is intended to be used with a specific types of suturing needle, sutures, and anchors, which will be provided in sterile packages to be used immediately after opening to preserve sterility. The suturing needle, sutures, and anchors are to be automatically loaded into the device, which may comprise two hinge-attached arms with blunt-ended tissue-piercing prongs located at the distal ends for catching and everting of the tissue surrounding an open wound. When the arms are squeezed together by one hand of the user, the prongs will bring the tissue edges together.

Once the edges have reached a fixed distance, further squeezing of the arms of the device will cause an initially internalized needle to emerge from the driver arm with attached suturing material and reach a pre-loaded anchor placed at the receiver arm. The needle will push through the anchor and retract back into the driver arm, leaving the suturing material inside the anchor. As the needle is being retracted, a fastening mechanism on the receiver arm will fasten an anchor over the suturing thread, hence securing the thread at a fixed distance from the thread's initial end.

By anchor, we mean any type of object that can be pierced or entered by a needle and may securely hold suture thread without slippage. The anchor may comprise an opening to allow a needle to penetrate and made of a material that can be compressed into small folds or ridges, i.e. a metal alloy crimp, as to tightly hold suturing thread between the folds or ridges. Alternatively, the anchor may also be made of a flexible or memory-retaining materials that can be pierced by a needle in such a manner that the suture thread being dragged through the anchor will not easily slip out of the anchor. The mentioned suture material can refer to any size of a nonabsorbable or absorbable suturing thread used by medical professionals for wound closure.

At the releasing of the squeezed device, the arms will release the edges of tissue and the suture will allow the tissue to relax into a position that abuts the edges of tissue, hereby promoting the healing of the wound.

An object of the invention is to have safety features such as a self-retracting needle that only emerges when the user is unable to access the needle in unsafe methods. Another object of the invention is to be sterile, portable, and either completely or partially disposable to promote its presence in hospitals, first aid kits and emergency medical vehicles. Sterilization and anesthetization of the wound are recommended prior to using the invention as such functions are not incorporated within the device. The device may be altered or scaled to allow for veterinary use, external wound closure, or internal wound closure, among other procedures.

BRIEF DESCRIPTION OF THE DRAWINGS

FIG. 5 illustrates the side view of the hollow driver arm of the first embodiment.

FIG. 6 illustrates the cross-sectional side view of the hollow driver arm of the first embodiment.

FIG. 58 illustrates the section view of the crimped anchor loading mechanism of the second embodiment.

FIG. 59 illustrates the magnified view of the crimped anchor loading mechanism of the second embodiment.

DETAILED DESCRIPTION OF THE DRAWINGS

Figure 69:
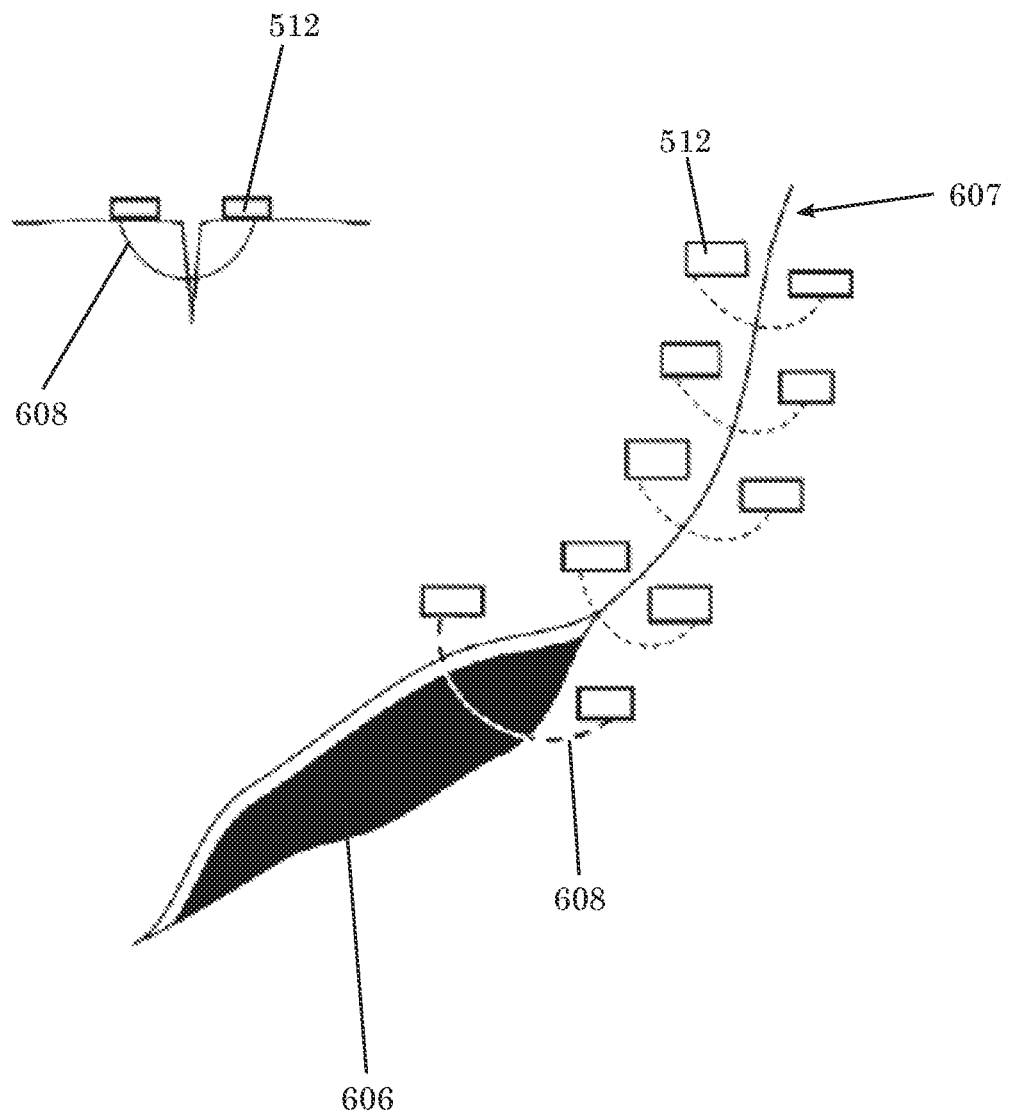
FIG. 69 illustrates the expected result of using the second embodiment to suture a wound.

Description of the invention will now be given with reference to the attached FIGS. 1-69. It should be understood that these figures are exemplary in nature and in no way serve to limit the scope of the invention, which is defined by the claims appearing hereinbelow.

Figure 1:
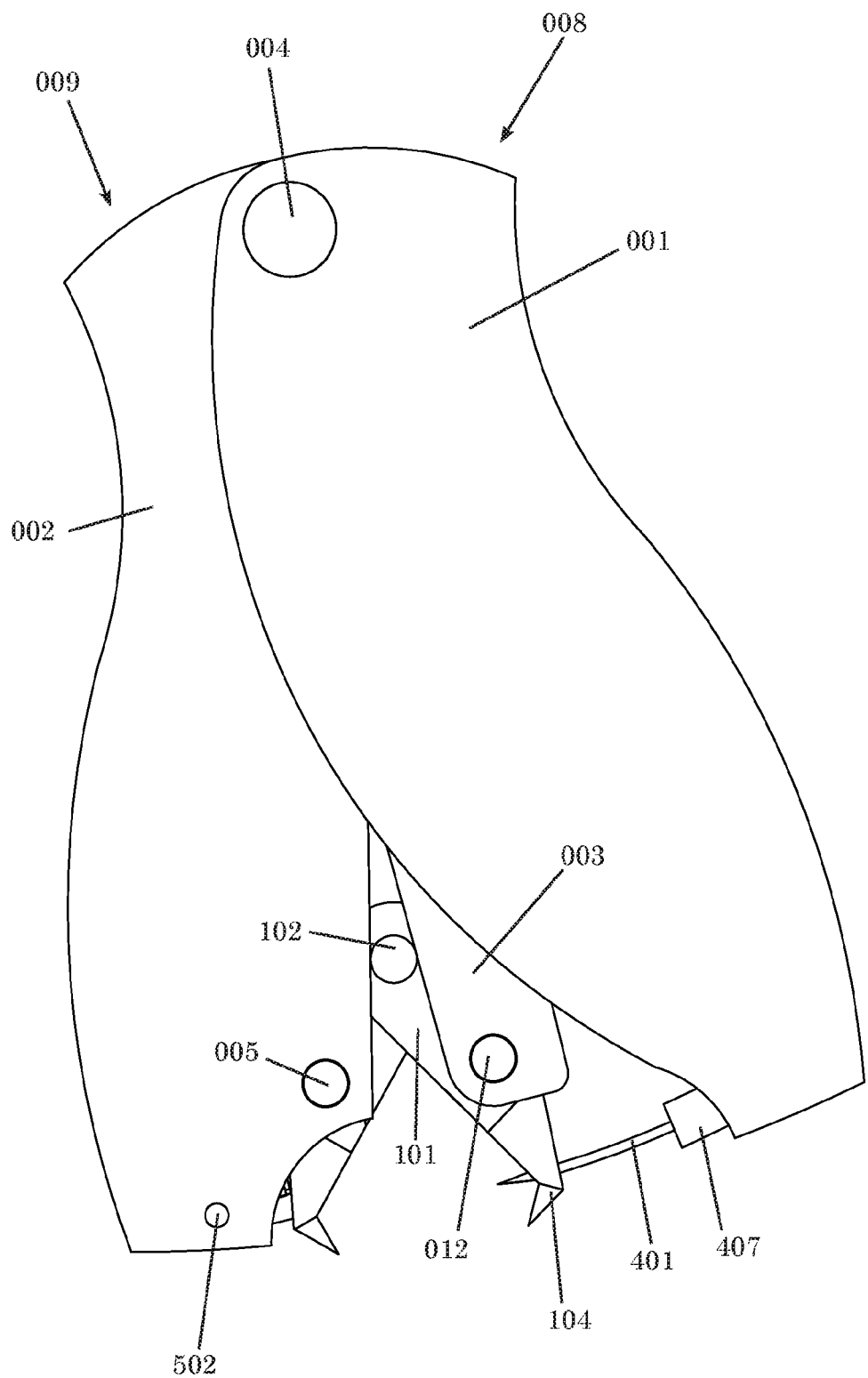
FIG. 1 illustrates the frontal view of the first embodiment in its open configuration.

A first embodiment, comprising tissue-piercing prongs and a reusable needle is described in FIG. 1. Both the driver arm 001 and the receiver arm 002 of FIG. 1 can be, in part or in whole, straight, curved, articulated, branched, or otherwise composed of multiple segments. In one embodiment, they are not longer than a human hand, for example, from about 5 cm to about 10 cm or 20 cm. In one feature, the arms 001 and 002 are lightweight. This ensures that the suturing device of FIG. 001 can be held comfortably in one hand and operated with one hand.

Figure 2:
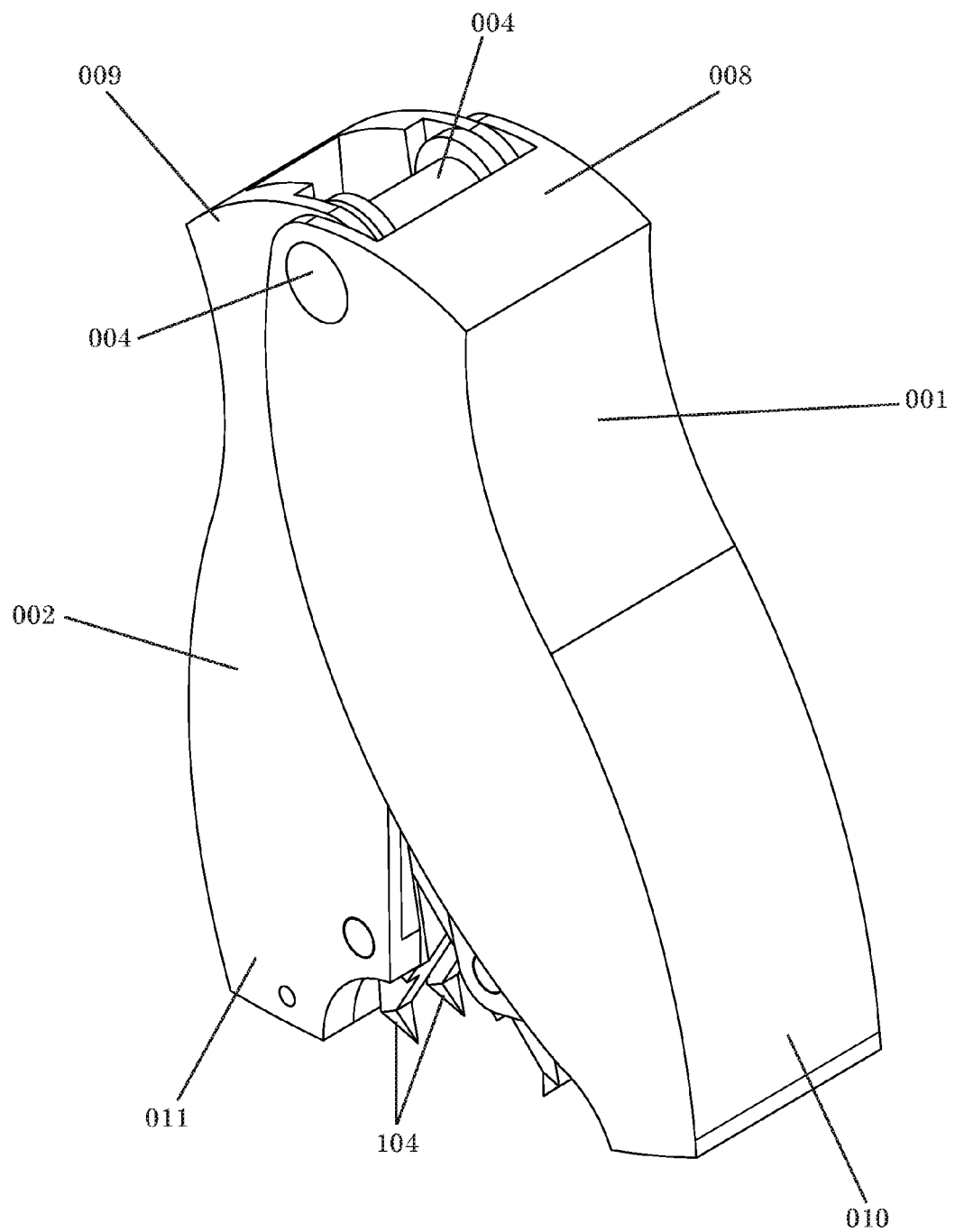
FIG. 2 illustrates the auxiliary view of the first embodiment in its open configuration.
Figure 3:
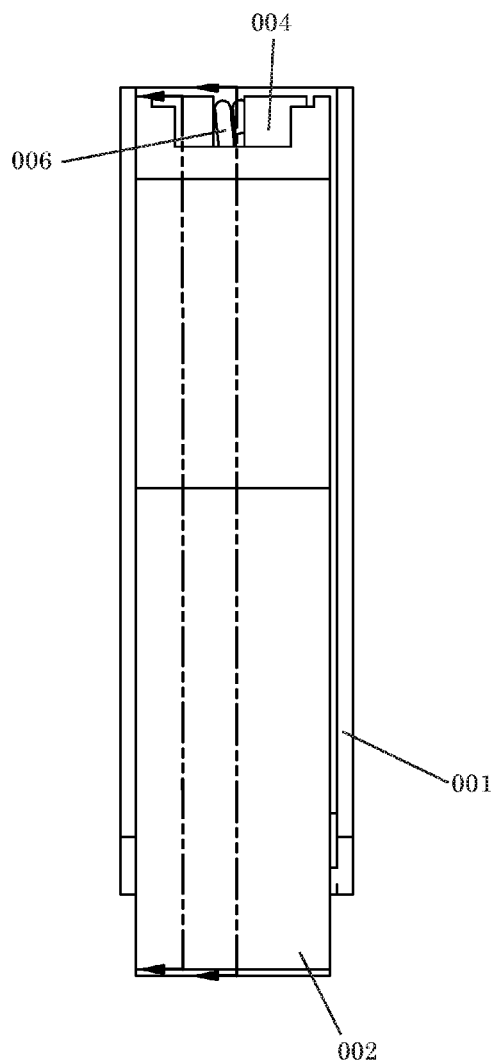
FIG. 3 illustrates the side view of first embodiment.
Figure 4:
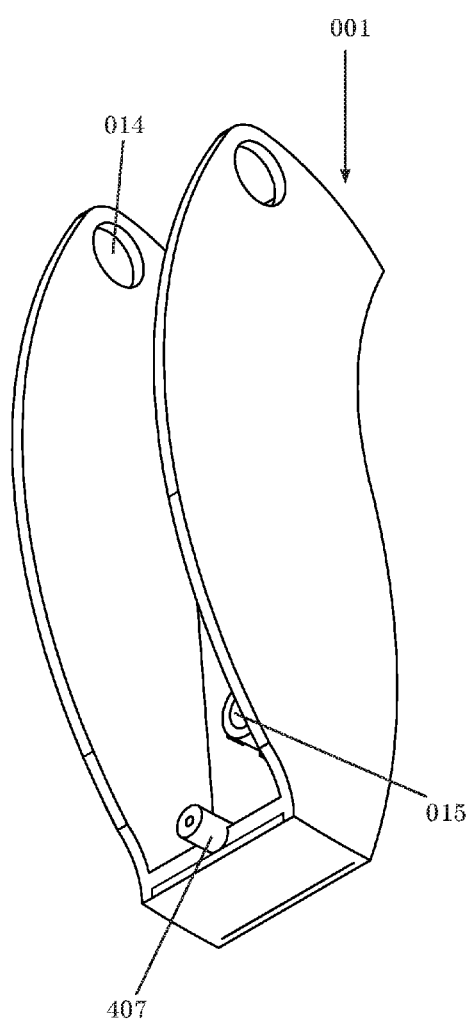
FIG. 4 illustrates the auxiliary view of the hollow driver arm of the first embodiment.
Figure 7:
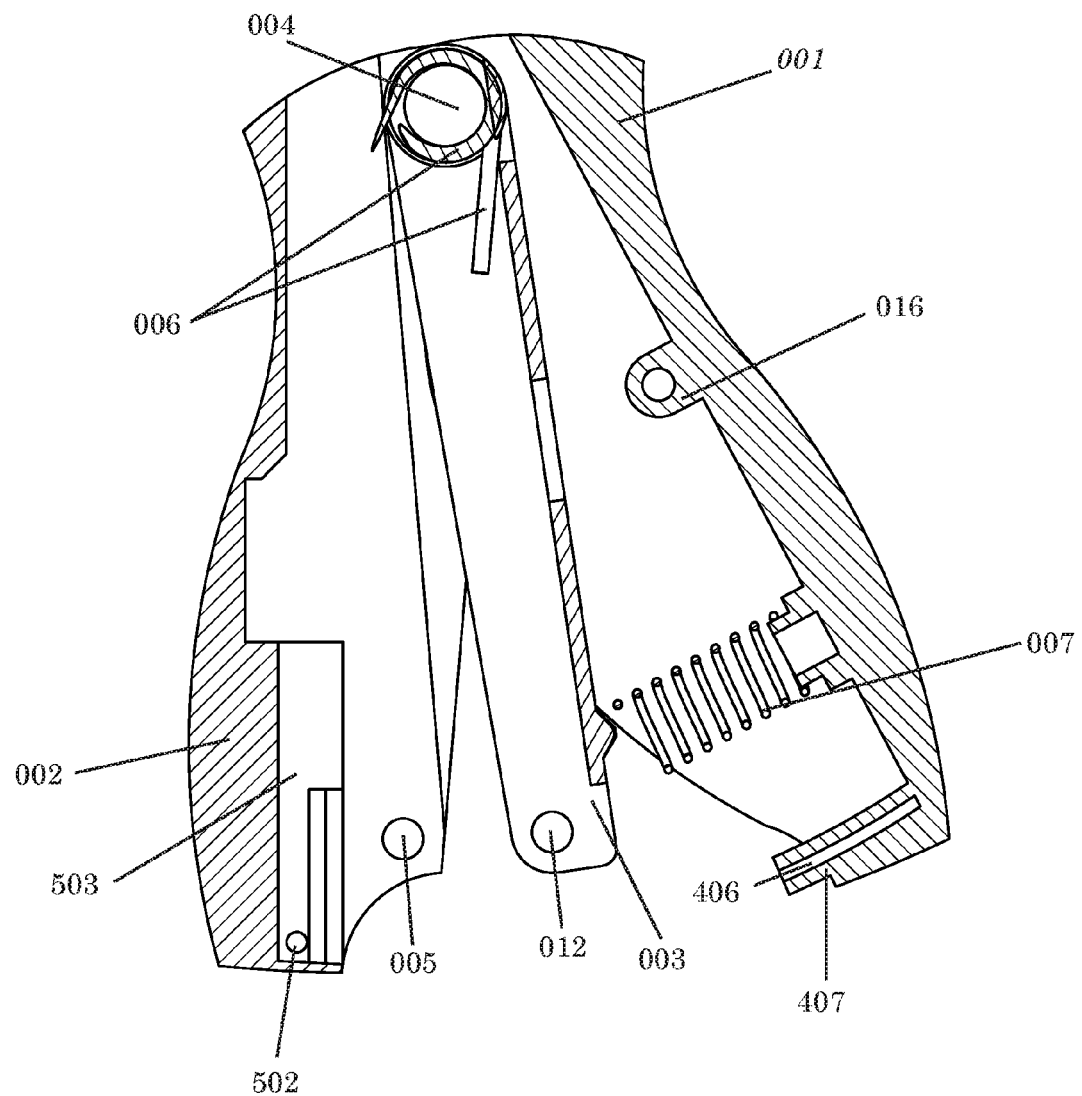
FIG. 7 illustrates the cross-sectional frontal view of the first embodiment in its open configuration.
Figure 9:
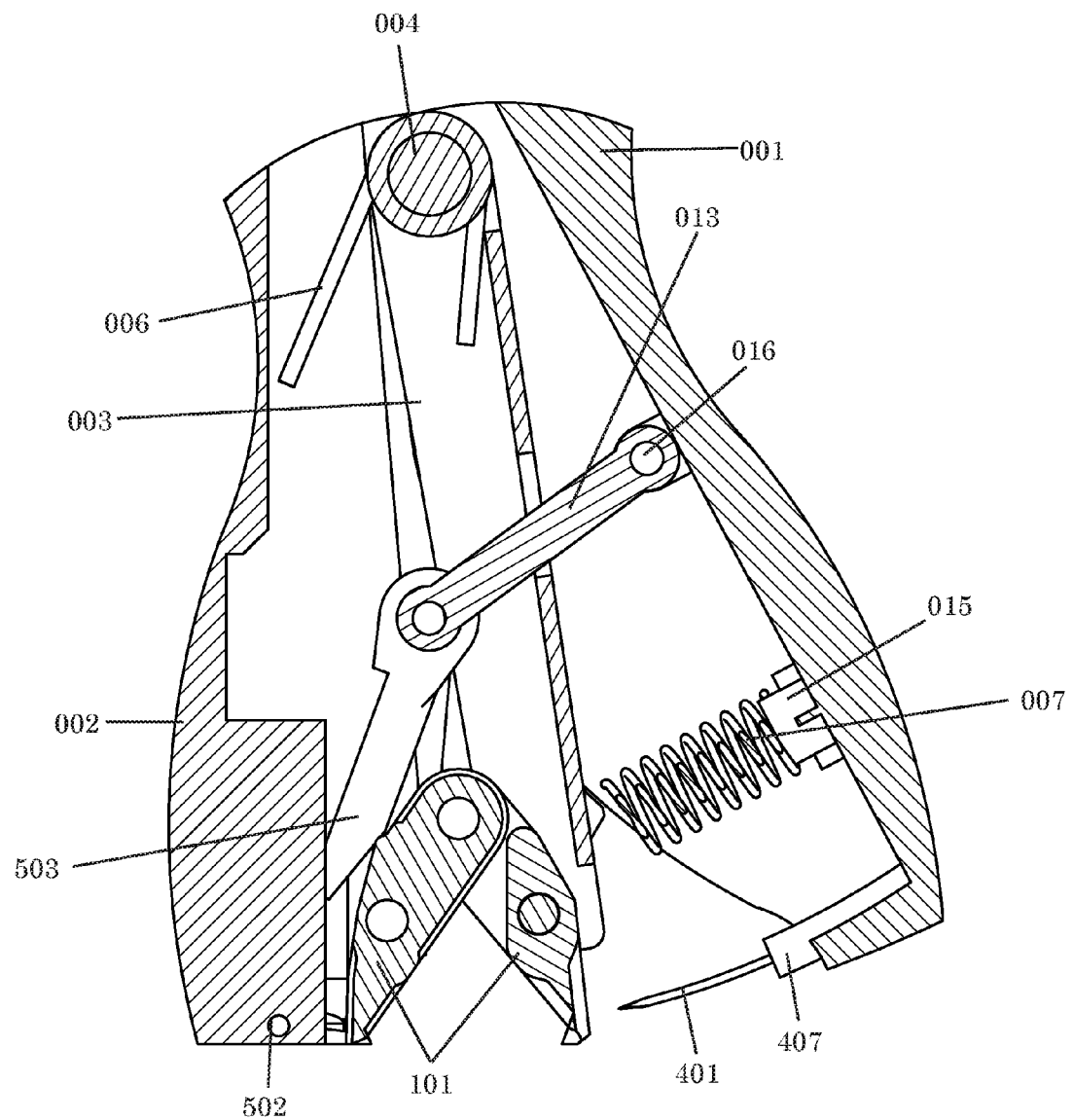
FIG. 9 illustrates the cross-sectional frontal view of the first embodiment including the fastener.
Figure 10:
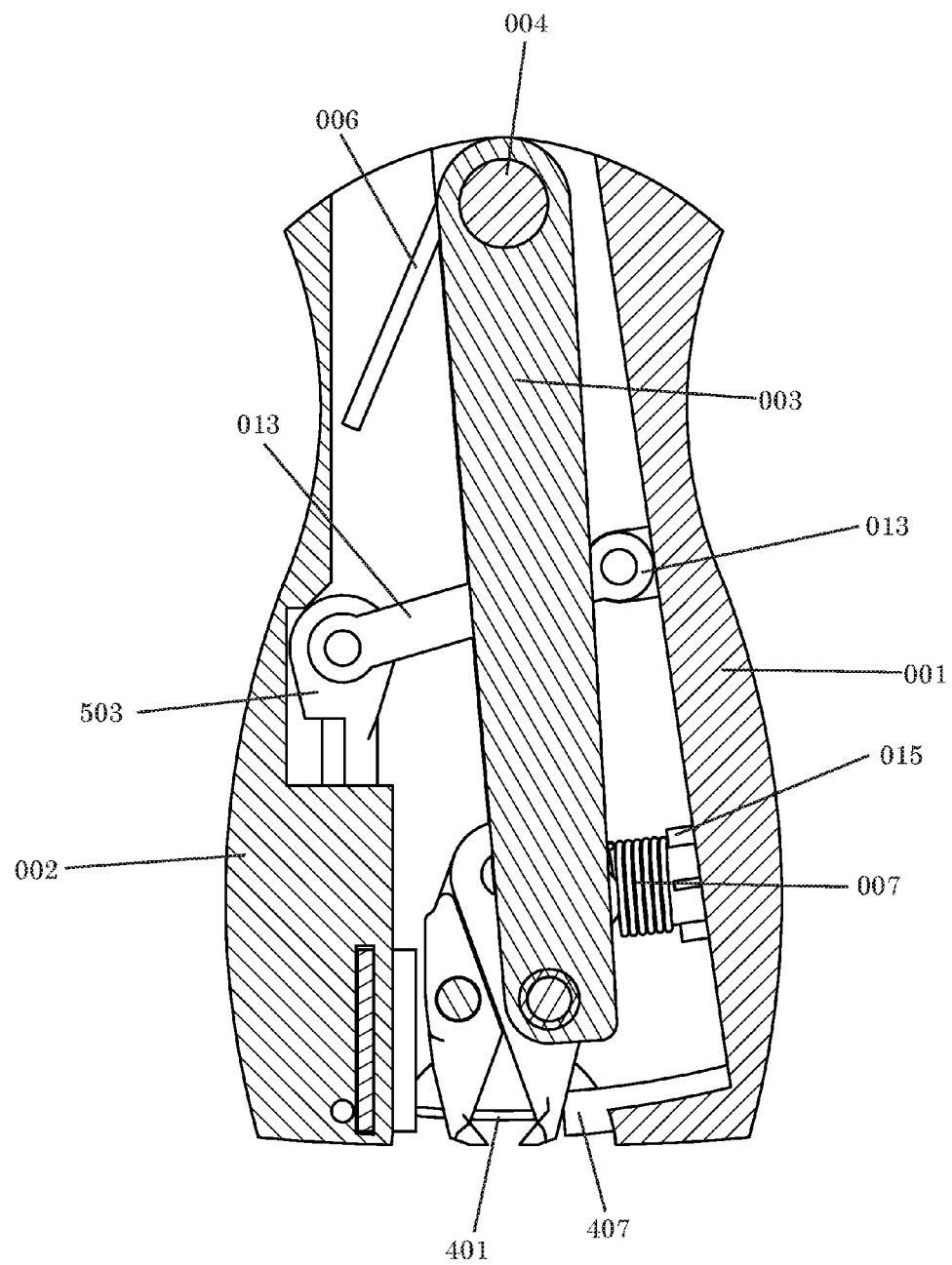
FIG. 10 illustrates the cross-sectional frontal view of the first embodiment in its closed configuration.
Figure 12:
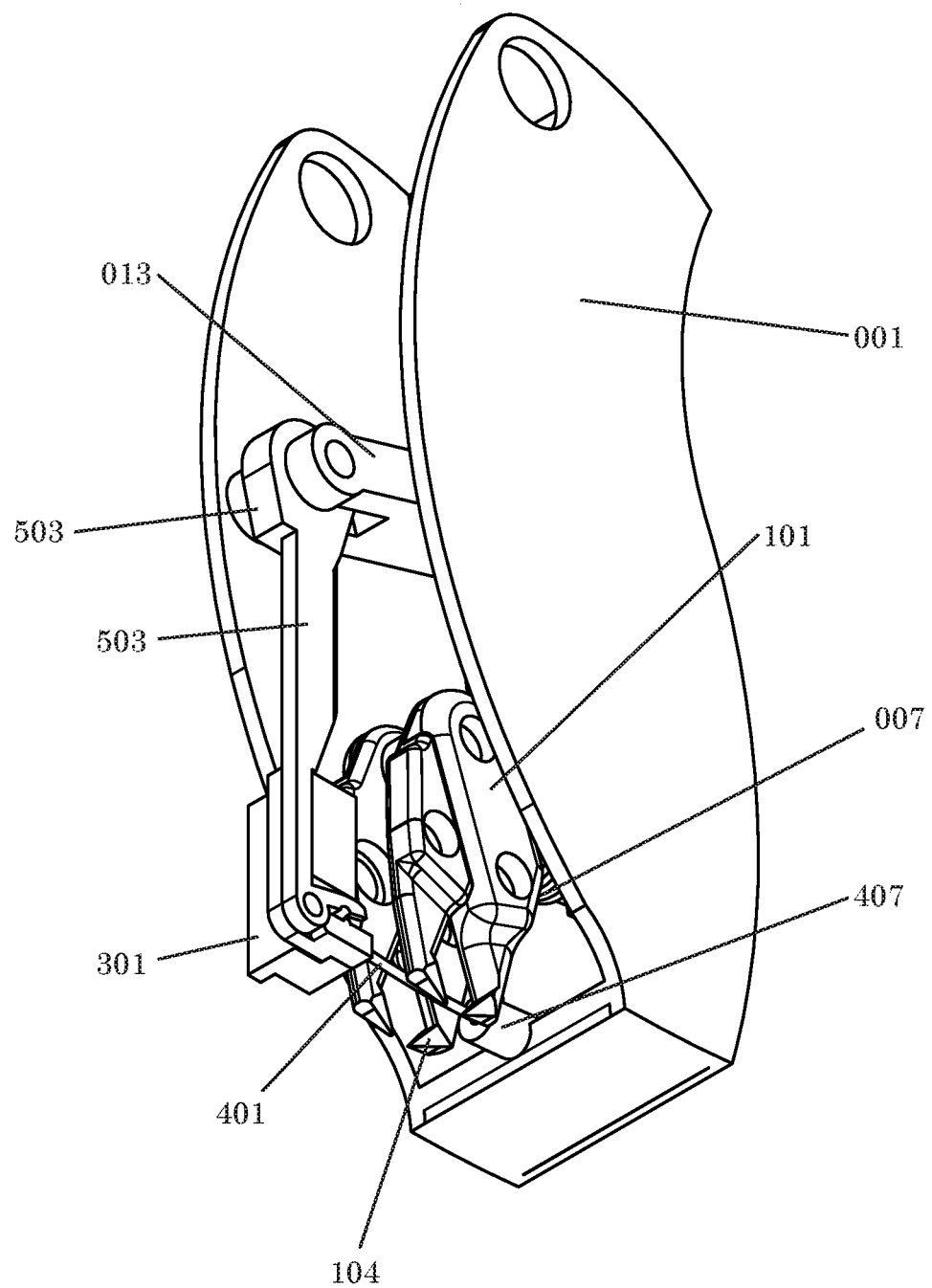
FIG. 12 illustrates the auxiliary view of the fastening mechanism of the first embodiment.
Figures 13, 14:
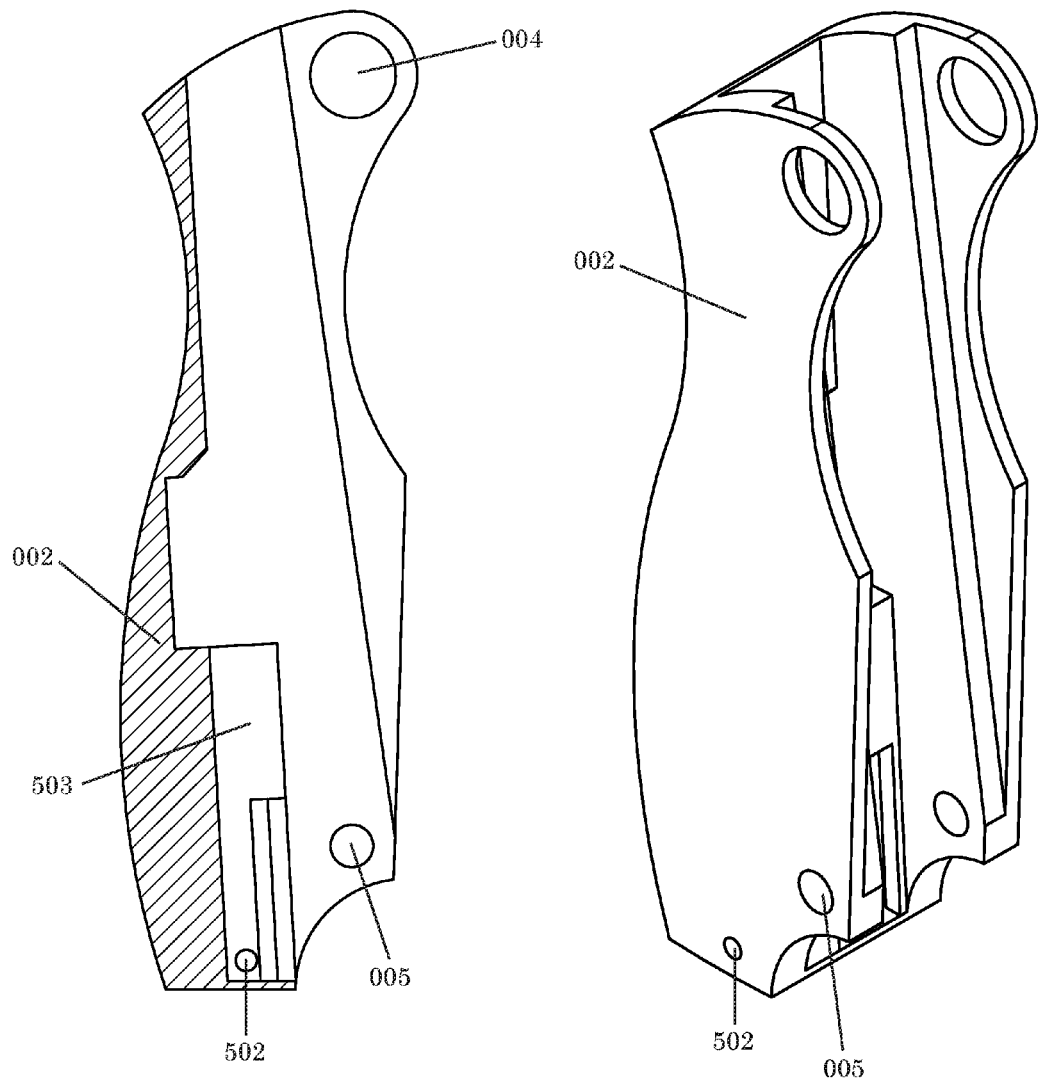
FIG. 13 illustrates the cross-sectional frontal view of the hollow receiver arm of the first embodiment.
FIG. 14 illustrates the auxiliary frontal view of the hollow receiver arm of the first embodiment.
Figure 15:
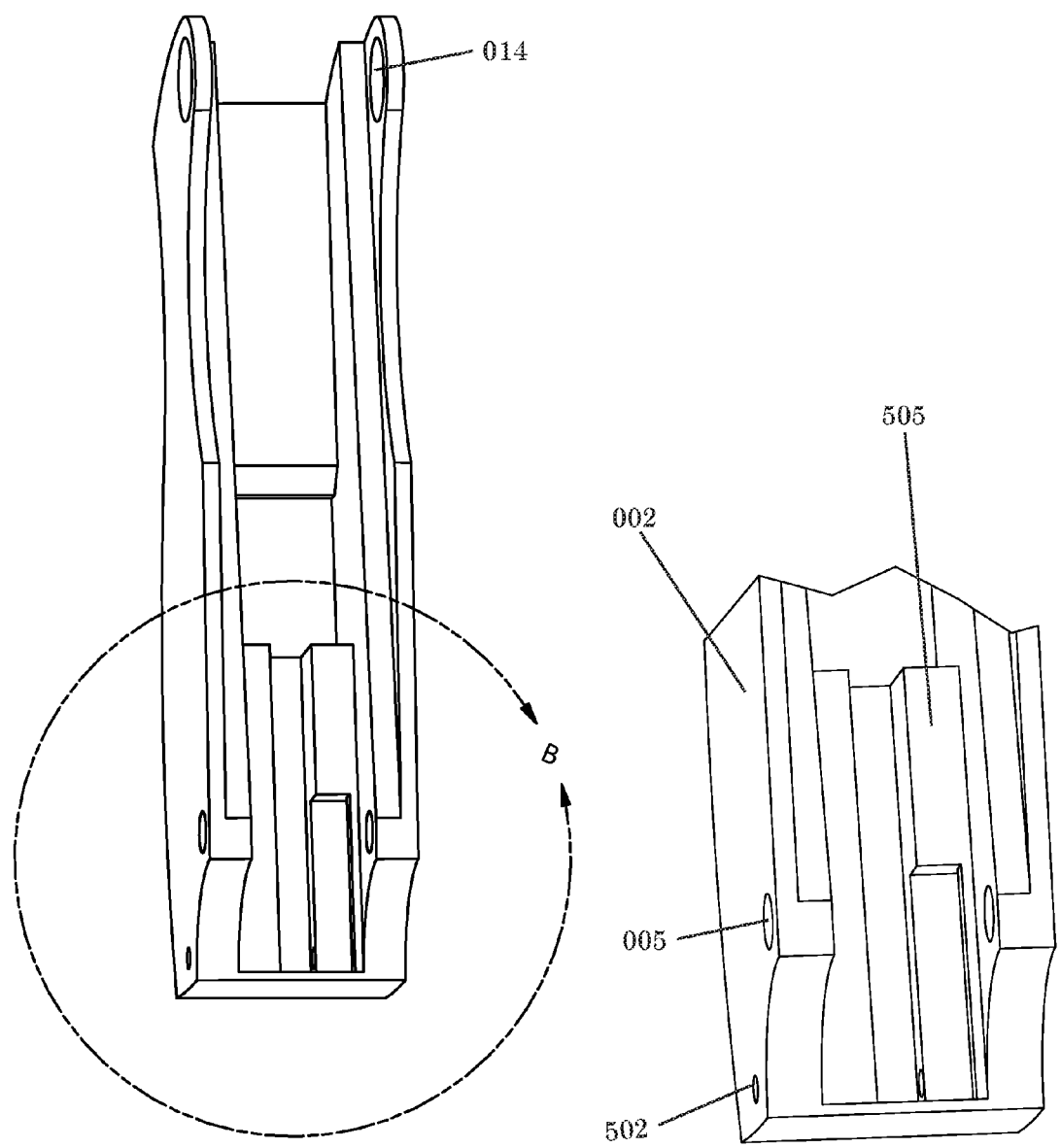
FIG. 15 illustrates the close-up of the distal end of the receiver arm of the first embodiment.

The driver arm 001 and the receiver arm 002 are generally of the same length and can be hollow or partially hollow or solid. For example, as seen in FIG. 2 the distal end 010 of the driver arm 001 and the distal end 011 of the receiver arm 002 are substantially hollow because they house the suture loading and the suture-fastening mechanism, respectively, as shown in FIGS. 12 and 15. However, one skilled in the art can readily realize other constructions for the arms 001 and 002. The cross-section of the arms 001 and 002 can have any shape provided they do not interfere with the suturing procedure. For example, the cross-section of either the driver arm 001 or the receiver arm 002 can be cylindrical or largely rectangular. As seen in FIG. 1, the proximal end 008 of the driver arm 001 and the proximal end 009 of the receiver arm 002 are connected by a hinge pin 004 that is inserted into the hinge clearance 014 (FIG. 4). The hinge pin 004 carries a torsion spring 006 of wound coils that tends to push the distal end of the driver arm 010 and the distal end of the receiver arm 011 away from each other as seen in FIG. 9. The torsion spring 006 is irreversibly attached to the arms of the device by a strong adhesive or an anchor.

Figure 8:
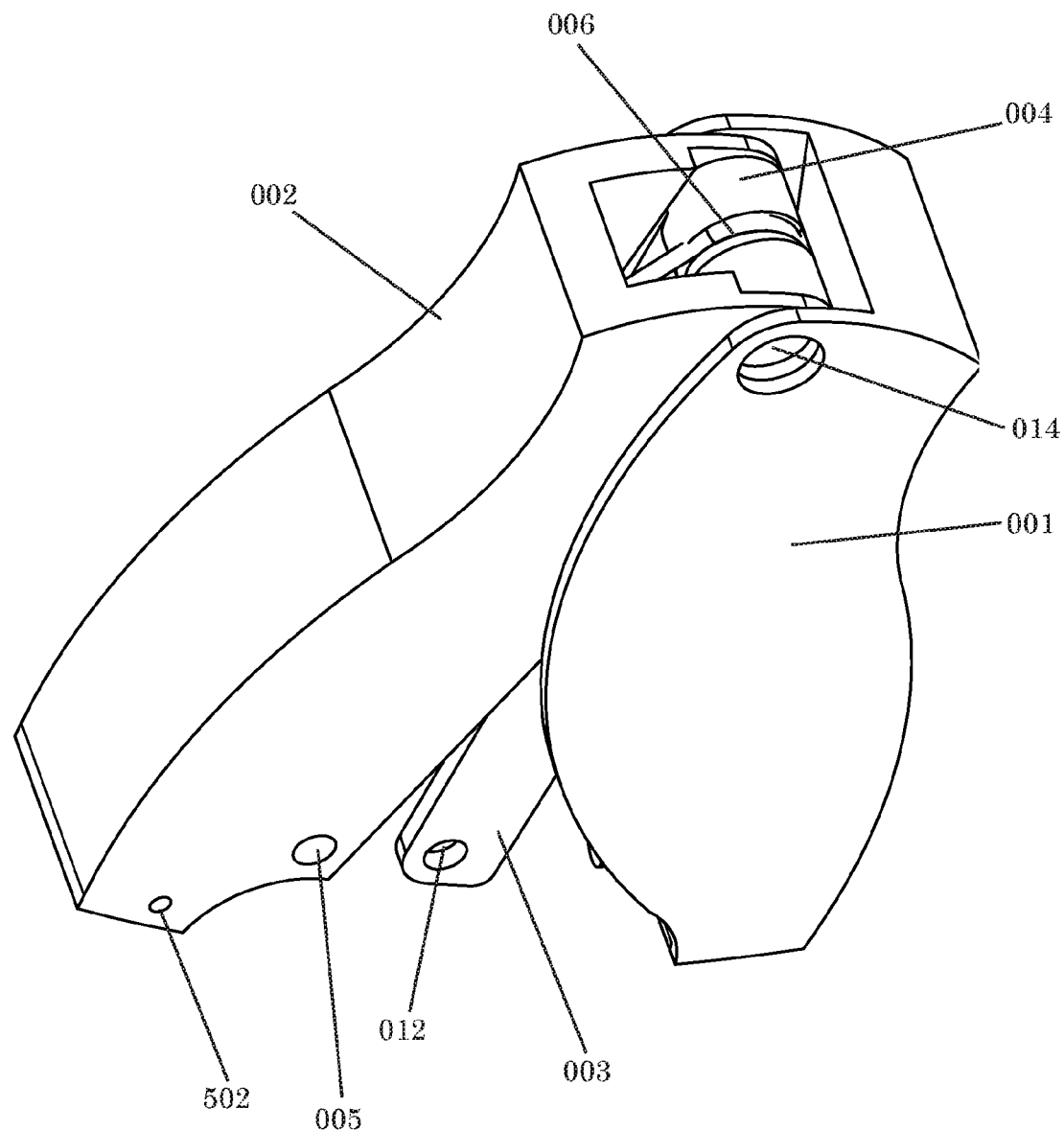
FIG. 8 illustrates the auxiliary top view of the first embodiment in its open configuration.

The driver arm 001 and the middle arm 003 of FIG. 8 are connected by a biasing coil spring 007 that is fixed over the spring holder 015 (FIGS. 4-6 and 9-11) and resists the squeezing of arms 001 and 002 until a physical contact point is reached. In the preferred embodiment, this physical contact point is set to be reached when the tissue-catching prongs 101 of FIG. 1 reach a maximum proximity. After this point, the device automatically impels a number of functions that proceed to completion, much like a commercial stapler.

Figure 11:
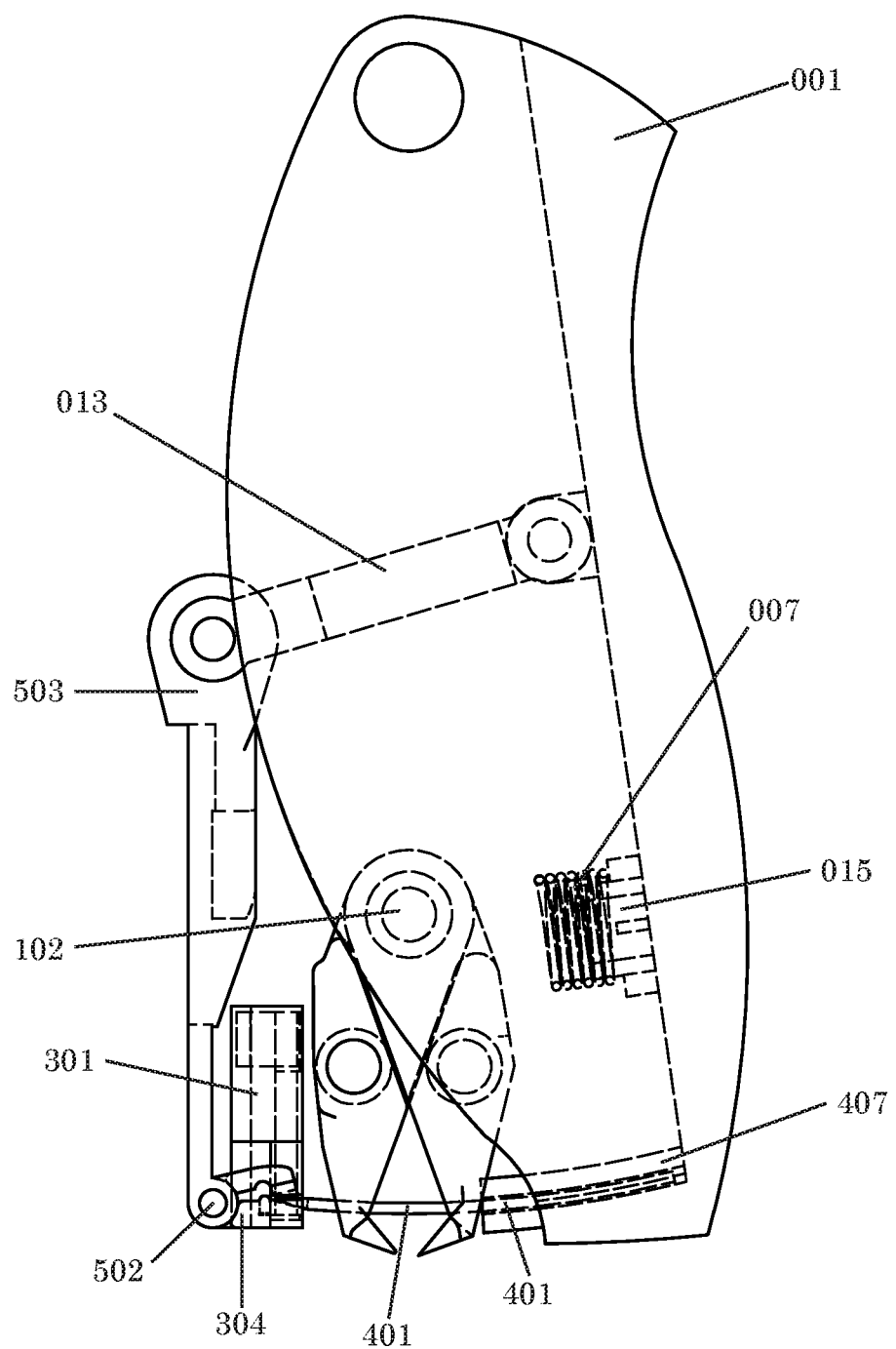
FIG. 11 illustrates the hidden-line frontal view of the fastening mechanism of the first embodiment.
Figure 16:
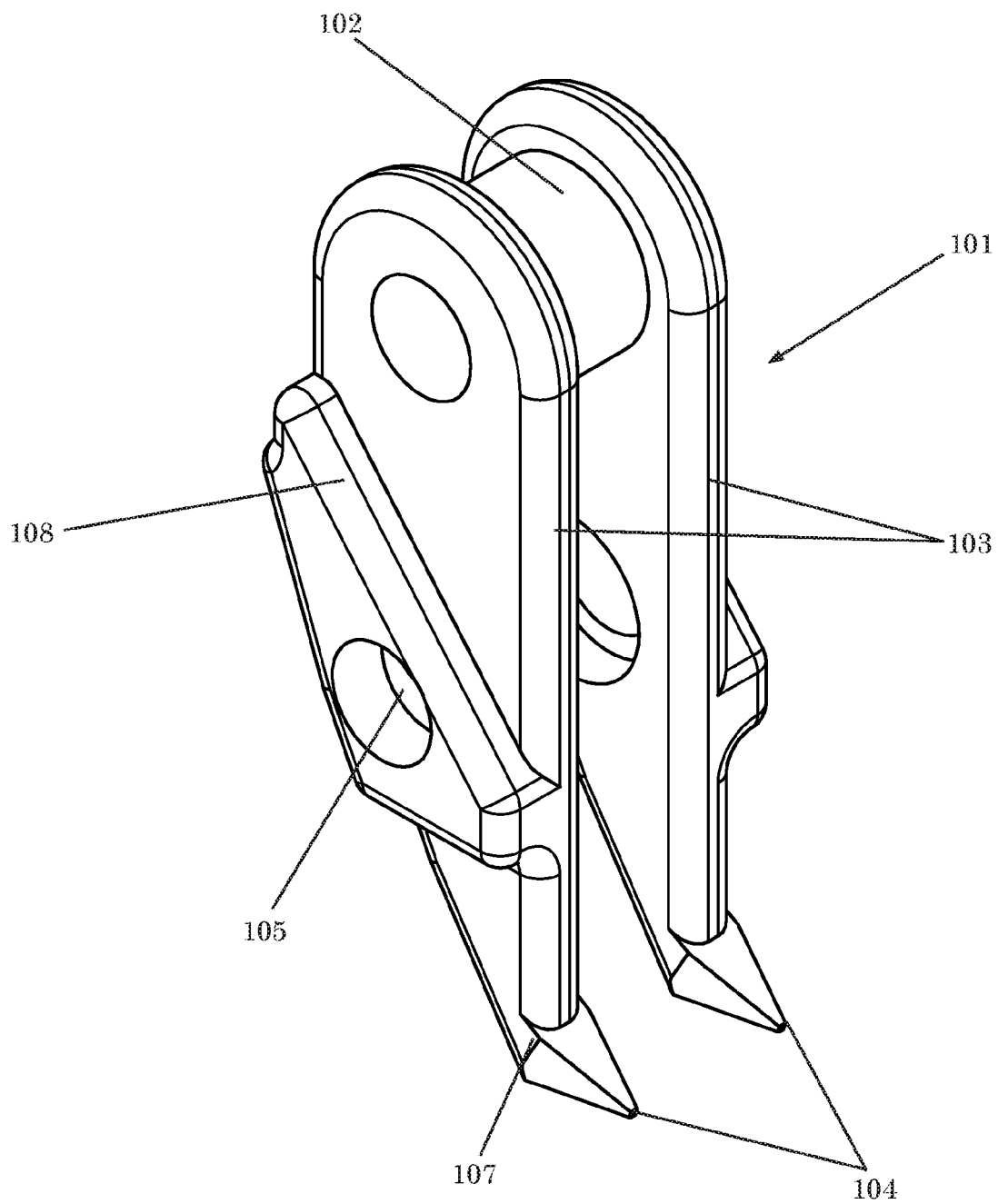
FIG. 16 illustrates the top auxiliary view of the blunt-ended tissue-indenting prongs of the first embodiment.
Figure 17:
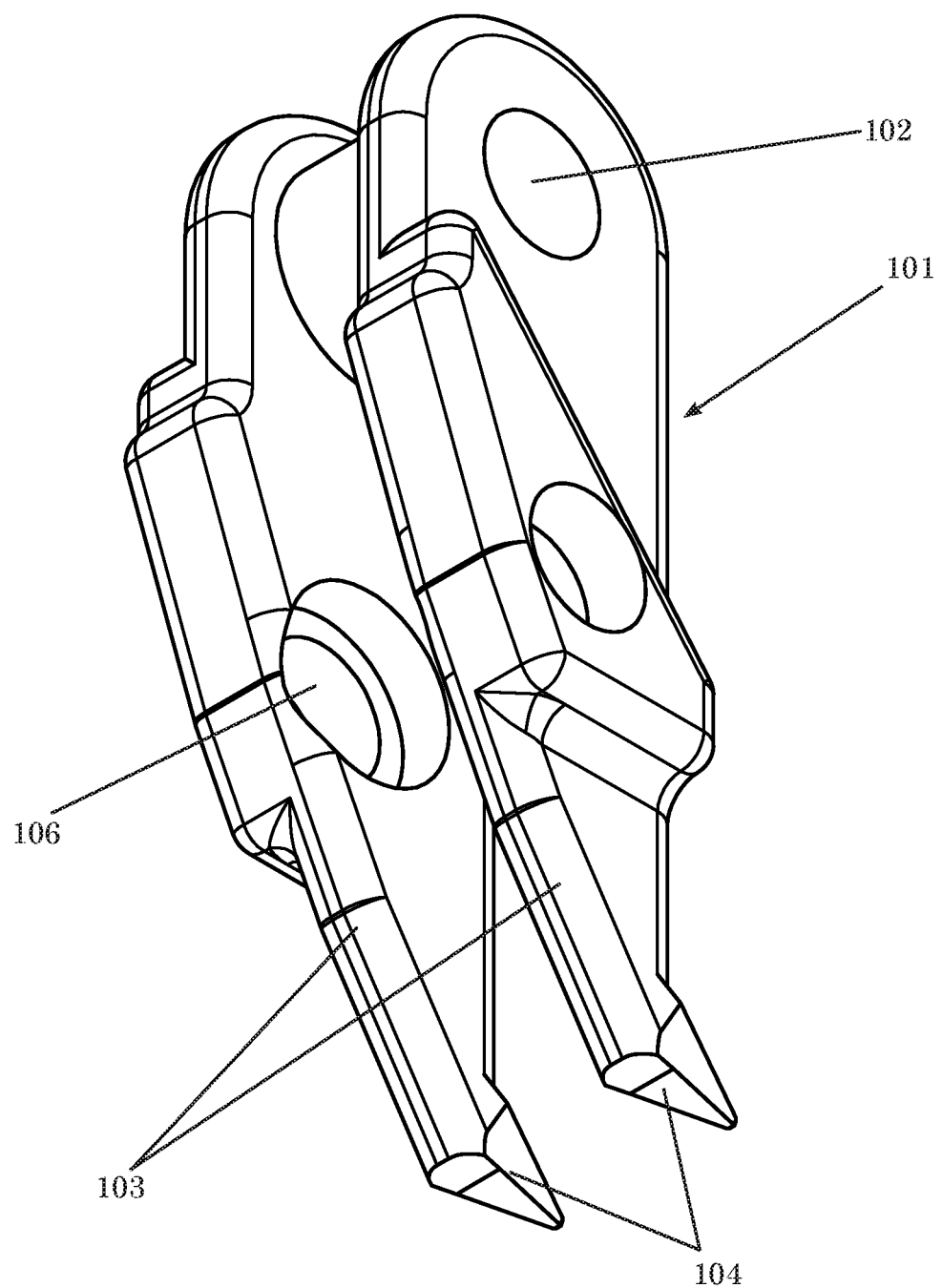
FIG. 17 illustrates the bottom auxiliary view of the blunt-ended tissue-indenting prongs of the first embodiment.

Shown in FIGS. 16 and 17 is one of two prongs 101 that bring the edges of the wound together in preparation for suturing. A prong 101 comprises two prong arms 103, each with blunt-ended tissue indenters 104 at the distal ends 107 of the prong arms (FIG. 6) that drag the two edges of tissue separated by a wound to a fixed position, where the tissue edges are everted so that the interior layers of tissue are abutted. To prepare the wound for suturing, the user must first align each prong 101 so that the distal ends 107 with the tissue-indenters 104 catch the tissue surrounding the wound. For the preferred embodiment, the tissue-indenters 104 should be placed approximately 5 mm outside the edge of the tissue on both sides of the wound. Once aligned, the device should be slightly pushed into the tissue until the surrounding flesh has been thoroughly caught by the tissue-indenters 104 and can be dragged to a median point by squeezing the driver arm 001 and the receiver arm 002 toward each other until they reach maximum compression. While the user squeezes the arms of the device, the prongs 101 will rotate toward each other about their common hinge 102 until the tissue-indenters are separated only by the tissue that they evert as seen in FIG. 16. The two prongs 101 are connected at their proximal ends by the hinge pin 102 as seen in FIG. 11. The prong hinge pin 005 near the distal end of one prong 107 connects the prong arms 103 to the fastener arm 002 while the hinge pin 012 near the distal end of the other prong 107 connects the second pair of prong arms 103 to the middle arm 003 (FIG. 1). The fastener secures the crimped anchor over the suture thread. In the preferred embodiment, the front axle clearances 105 of FIG. 16 are smaller in diameter than the rear axle clearances 106 (FIG. 17).

The two prongs 101 are identical except for that each prong has an extrusion 108 facing in the direction that complements the extrusion of the other arm 108 (FIG. 16). The two arms 103 of both prongs 101 are fitted together in alternating order so that the extrusions 108 fit together perfectly when the device is squeezed by the user. Shown in FIG. 1, the prongs 101 are attached to the receiver arm 002 and the middle arm 003 by hinge pins 005 and 012 that go through the hinges clearances 105 and 106 shown in FIG. 16 and FIG. 17, respectively. The middle arm 003 is indirectly controlled by controlling the driver arm 001. Therefore, the user does not directly handle the middle arm 003 despite using the middle arm 003 to evert the surrounding tissue of a wound. The device has been designed so that the distal ends 107 of the prongs can be set to a maximum distance from each other, depending on the nature of the wound being sutured. Suturing of abnormally wide wounds can result in tension of the internal tissue and organs under the wound and may cause further damage.

Figure 18:
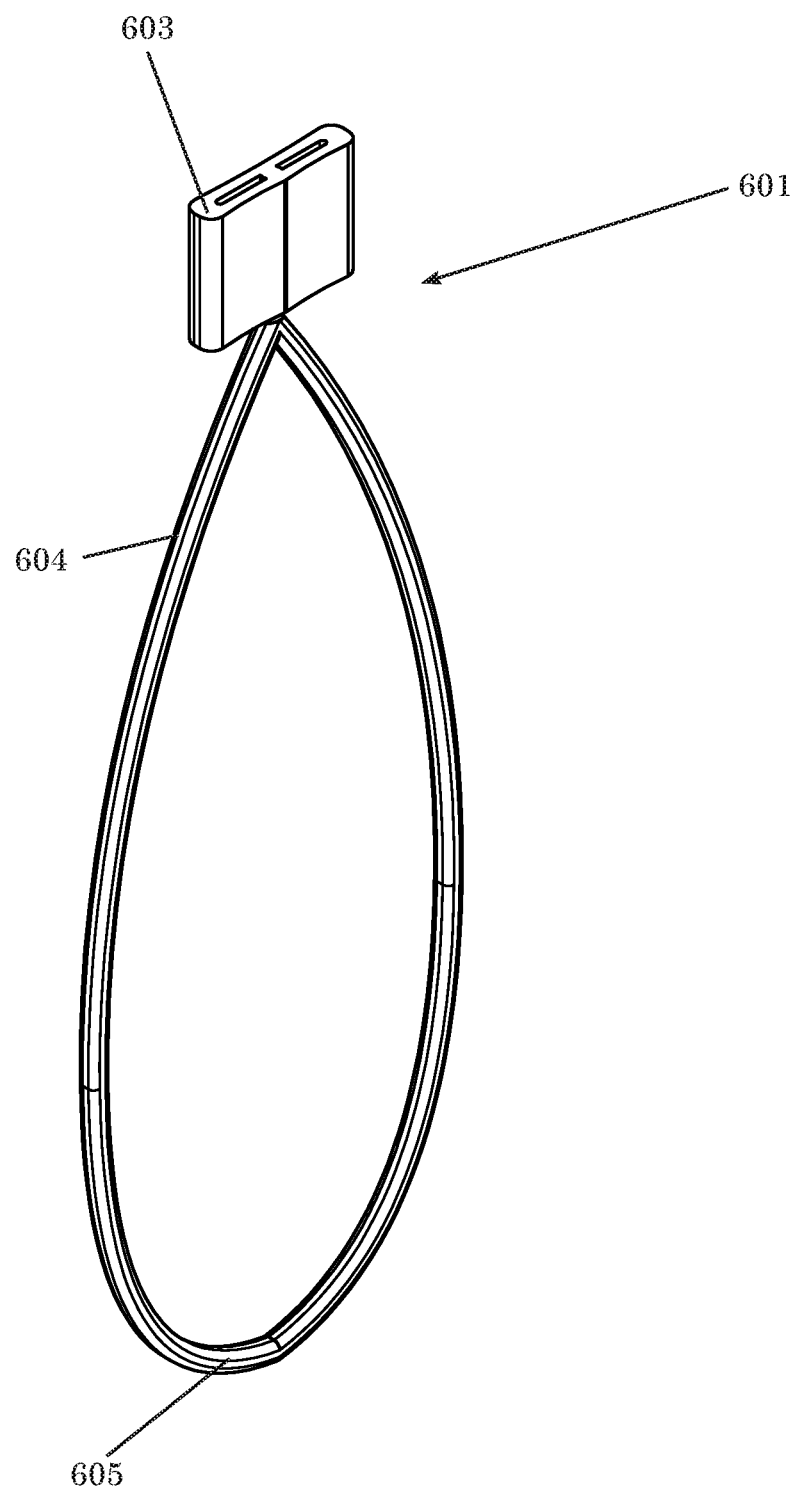
FIG. 18 illustrates the suture unit to be used by the first embodiment.

The surgeon may select a suture unit 601 with suture material 604 of varying the length, diameter, and characteristics of the suture depending on the nature of the wound in question. In one embodiment, the suture unit 601 consists of exactly 32 mm of suture material 604 that is brought together into a loop, where a unit is a structure, series, or process the end of which is connected to the beginning. The ends of the suture material 604 are connected by a fixed anchor 603 that has been fastened over the ends of the suture material 604 as shown in FIG. 18. The suture material 604 and the fixed anchor 603, form the suture unit. The length between the anchored end of the suture unit 601 and the looped end of the suture unit 605 can be altered as suitable for the nature of a given wound. In the preferred embodiment, the device should hold at least ten of the described suture units 601 in the suture unit loader 201 of FIG. 23, from which the needle 401 of FIG. 19 will catch them to be used for suturing.

Figure 19:
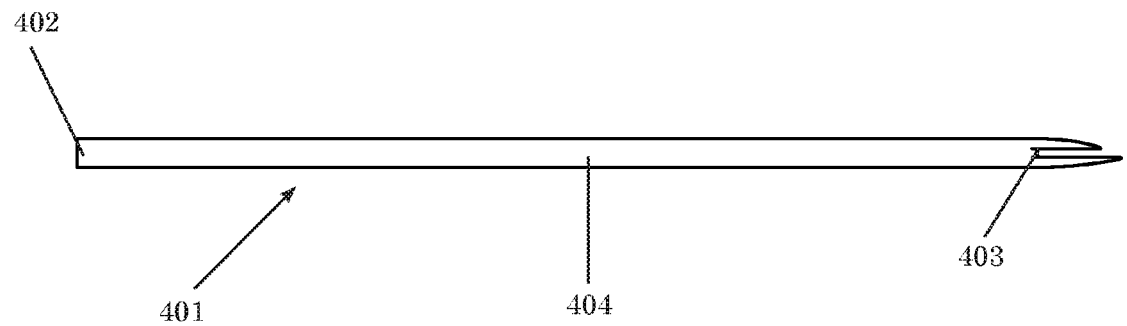
FIG. 19 illustrates the top view of a hooked needle to be used by the first embodiment.
Figure 20:
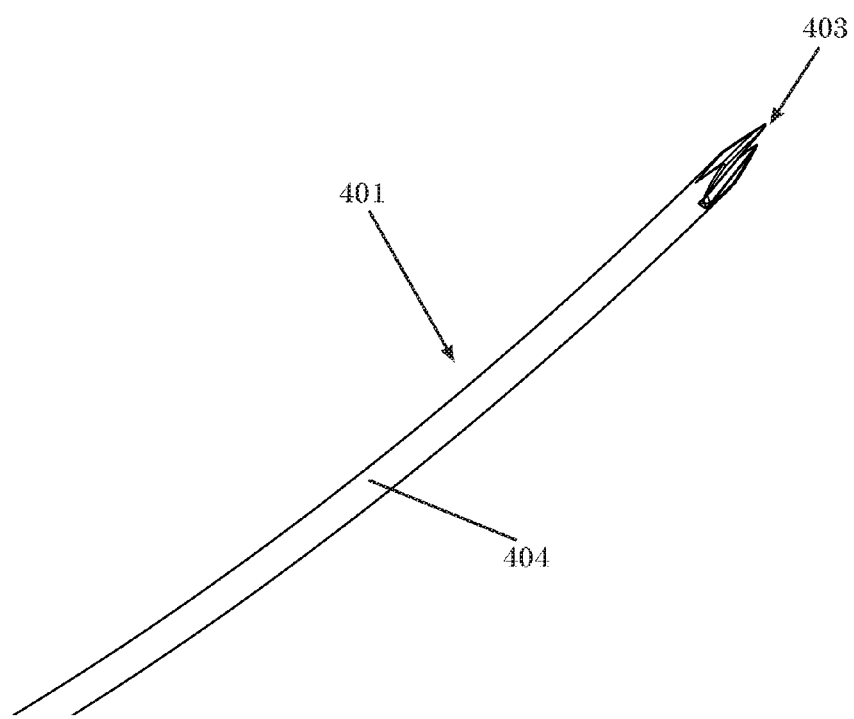
FIG. 20 illustrates the side view of a hooked needle to be used by the first embodiment.
Figure 21:
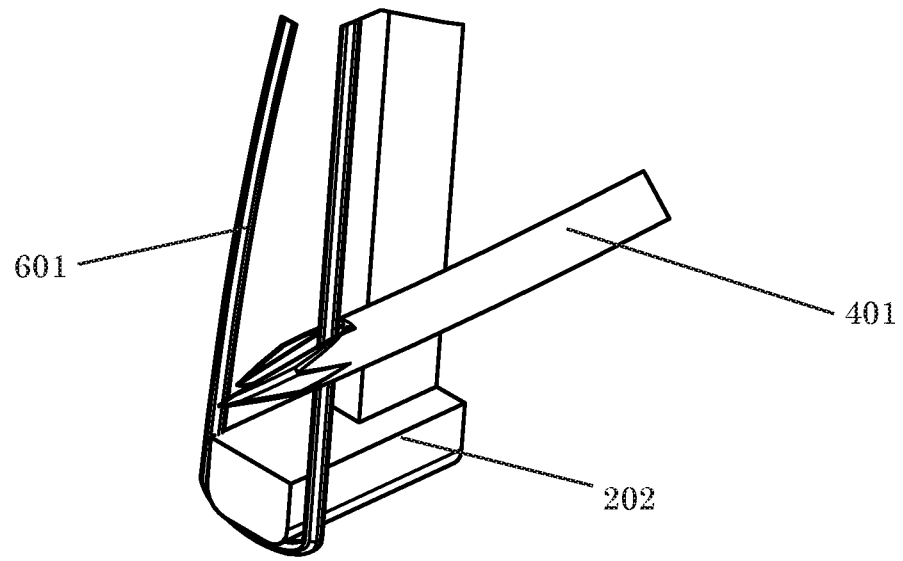
FIGS. 21 and 22 illustrate the catching of the suture unit by the needle of the first embodiment.
Figure 22:
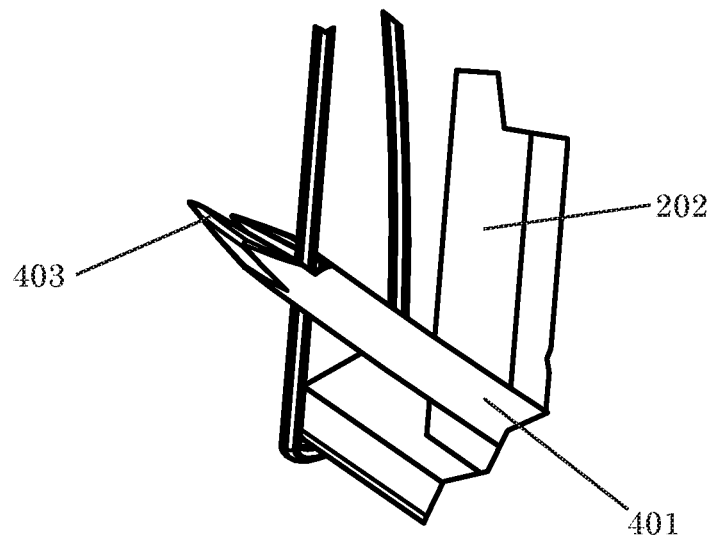

Referring now to FIGS. 19 and 20, a suturing needle 401 that can be used with the suturing device of the present application is described. FIG. 20 shows a suturing needle 401 with a curved shape comprising a non-penetrating, rectangular blunt end 402 and a sharp, penetrating pointed end 403 (FIGS. 19 and 20). As the needle 600 passes through a path that allows the hooked end 403 of the needle to catch a suture unit 601 at its looped end 605 (FIG. 18) from the suture unit loader 201. As shown in FIGS. 21 and 22, the hooked end 403 has a fork-like structure that is able to catch the suture material 604 and penetrate the everted edges of tissue cleanly without catching tissue inside the fork-like structure and tearing it. The blunt end 402 may be tapered such that the diameter at the blunt end 402 is smaller than the diameter of the needle shaft 404 (FIG. 20). That configuration facilitates the insertion of the blunt end 402 into the needle clasp 407 within the driver arm 001 to fill the needle cavity 406 shown in FIG. 6 prior to using the device.

Figure 23:
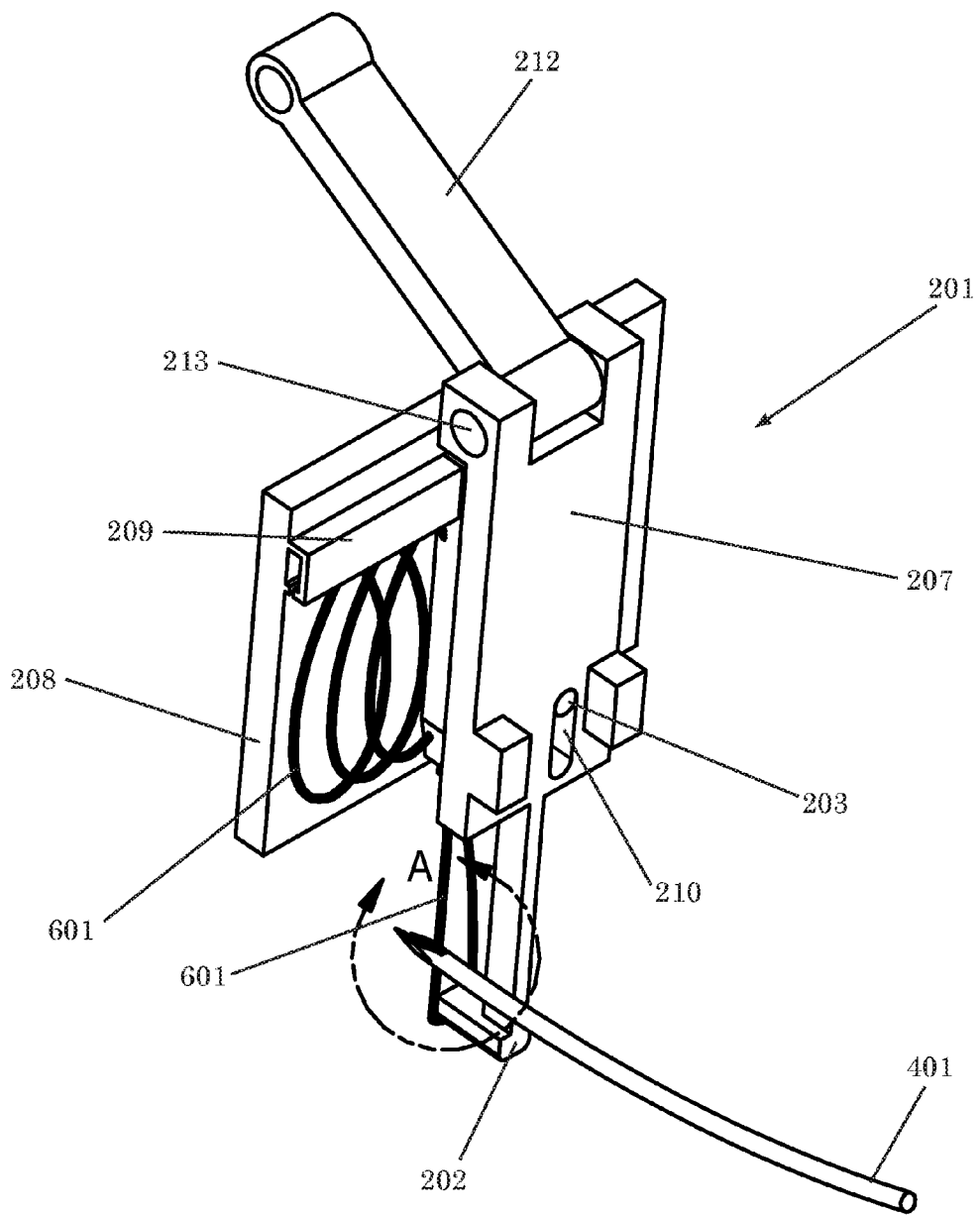
FIG. 23 illustrates the auxiliary view of the suture loading mechanism of the first embodiment.
Figure 24:
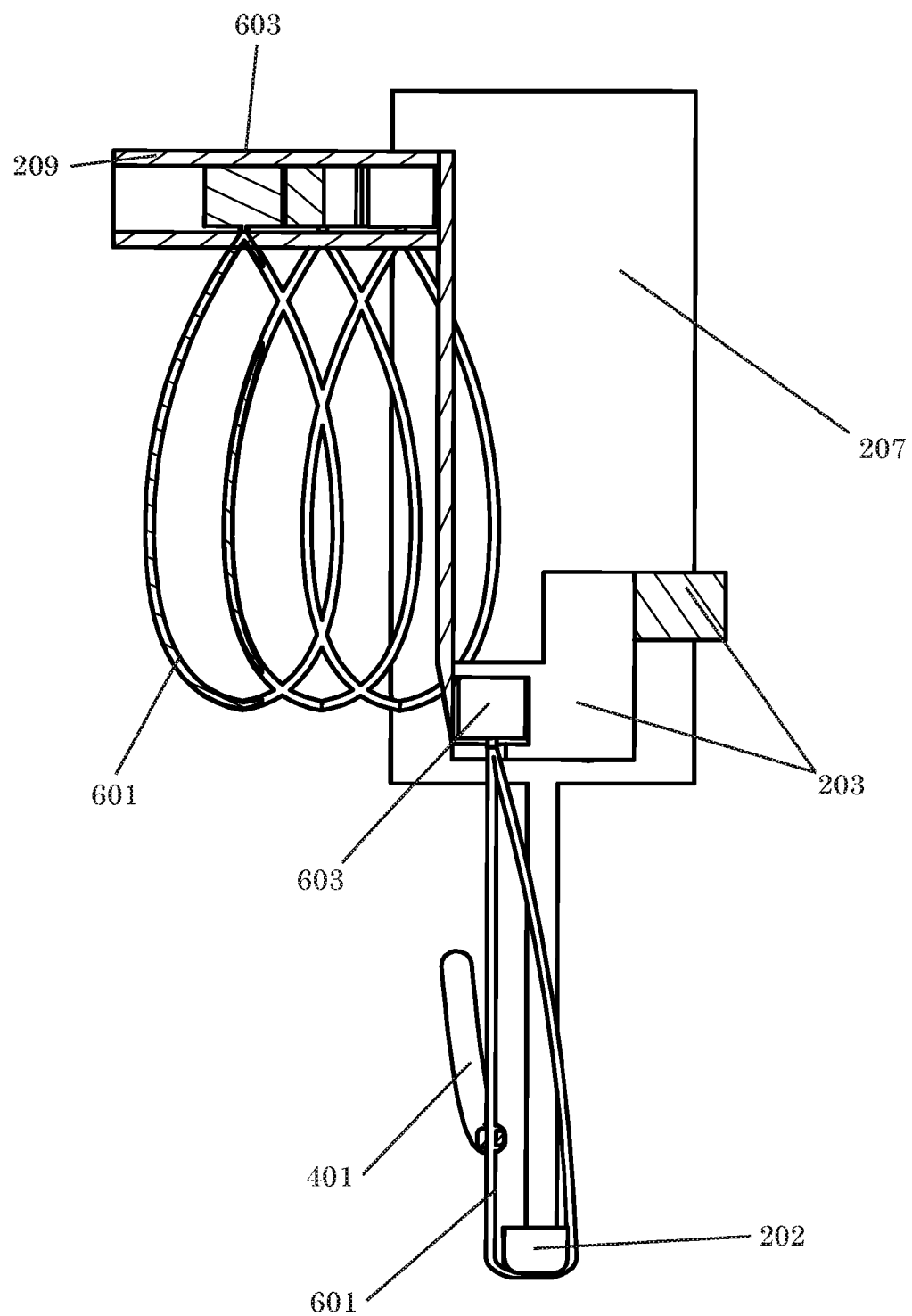
FIG. 24 illustrates the side view of the suture loading mechanism of the first embodiment.
Figure 25:
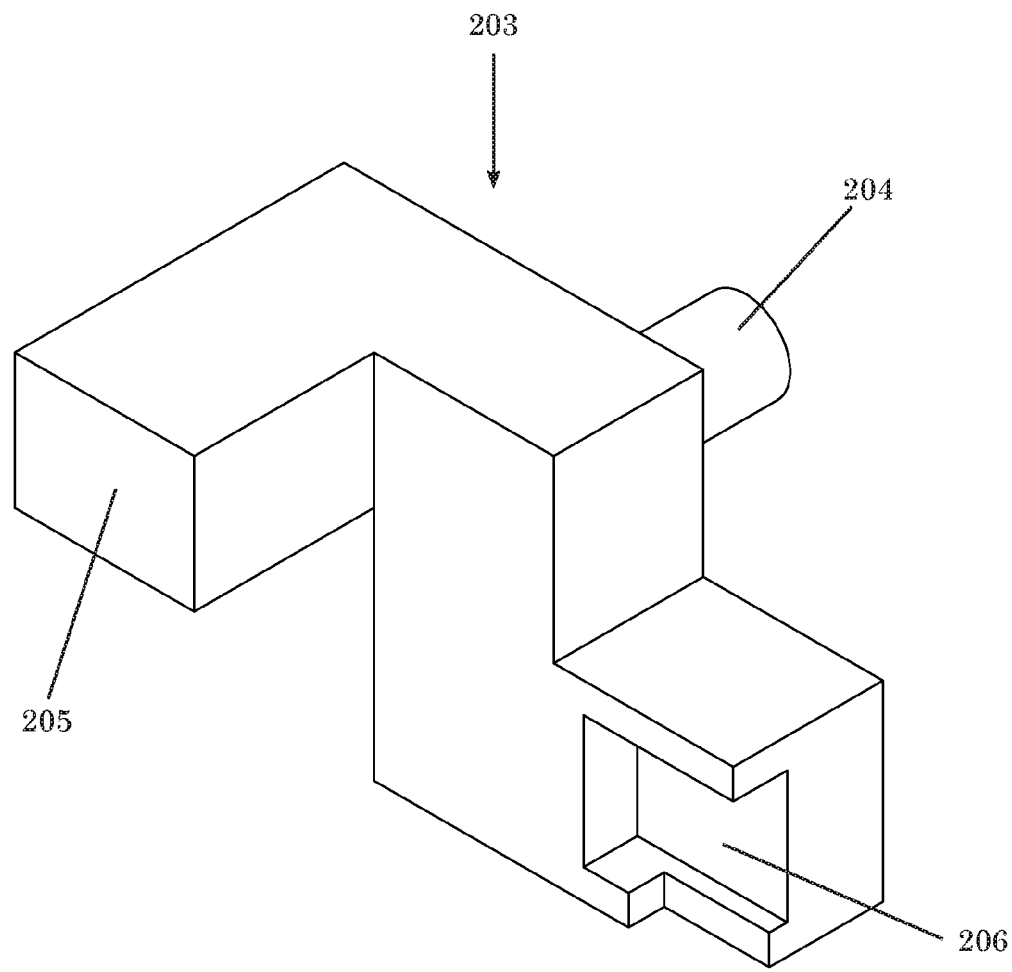
FIG. 25 illustrates the auxiliary view of the sliding pin used in the suture unit loading mechanism of the first embodiment.
Figure 26:
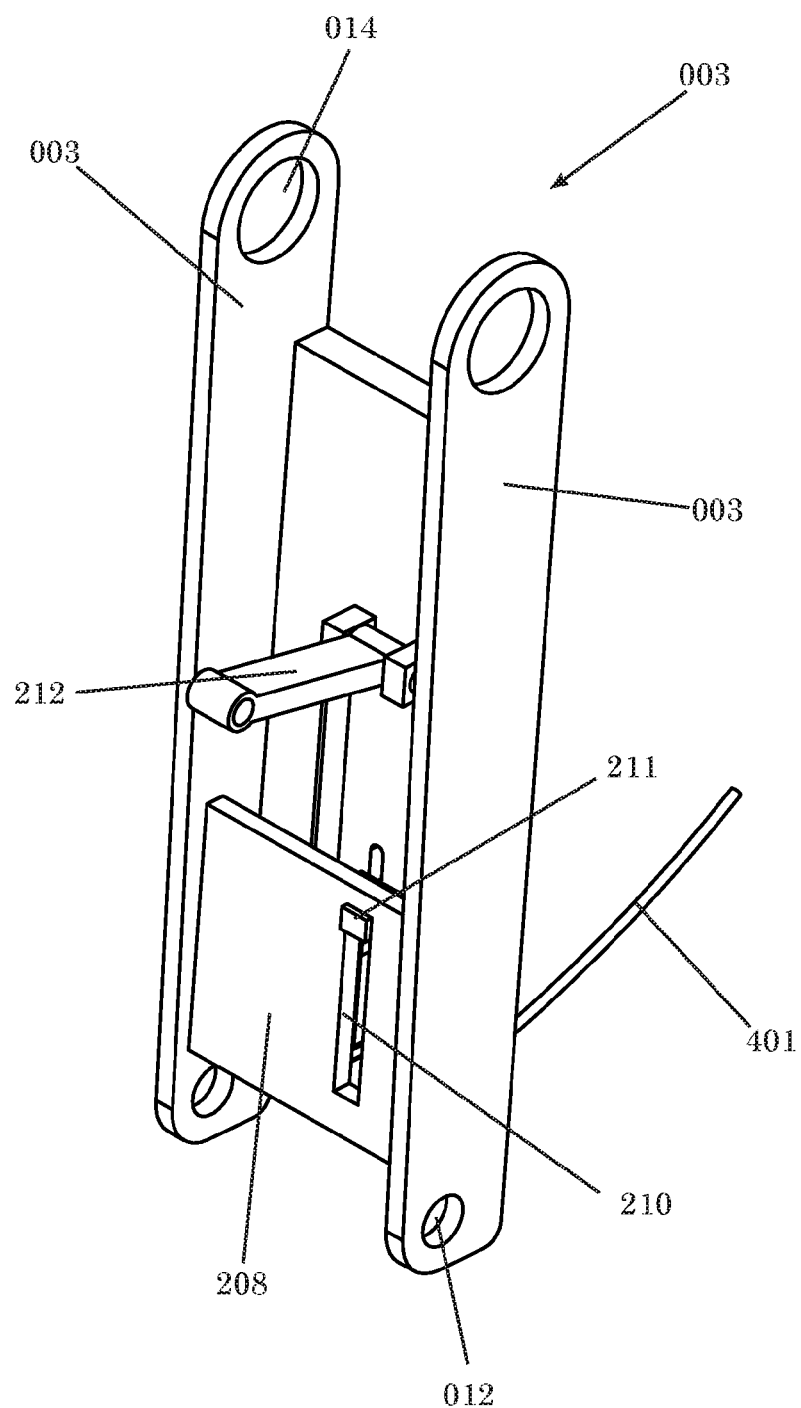
FIG. 26 illustrates the auxiliary view of the suture unit loading mechanism housed in the middle arm of the first embodiment.
Figure 27:
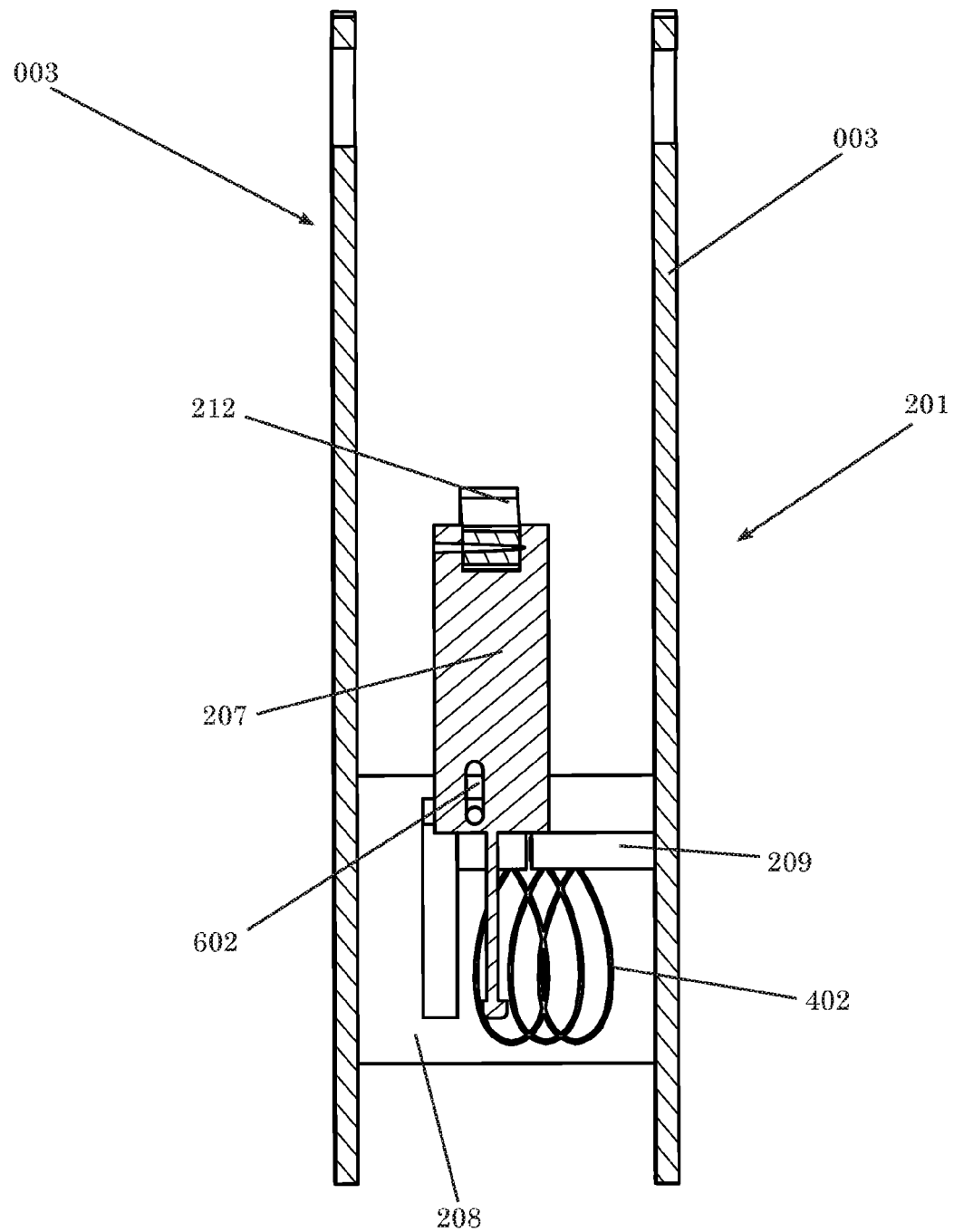
FIG. 27 illustrates the side view of the suture unit loading mechanism housed in the middle arm of the first embodiment.

As the device's arms are squeezed, the needle 401 passes through the middle arm 003, which houses the suture unit loader 201, to catch a suture unit 601 before entering the tissue. The suture unit loader 201 comprises suture units 601 that hang in the suture house 208 of FIG. 23 by their fixed anchors 603 (FIG. 24). The fixed anchors fit into a fixed anchor rail 209 shown in FIG. 23 that allows the suture loops 601 to slide within the suture house 208. As arms 001 and 002 are squeezed together, a loading arm 212 pivots about a loading arm hinge pin 213 FIG. 23. This pivoting motion pushes and pulls the driving plate 207, which shifts translationally to navigate the cylindrical front 204 of a sliding pin 203 through a front pin slot 210 (FIGS. 23 and 25). The movement of the sliding pin 203 catches a suture unit 601 from the fixed anchor rail 209 by sliding over a fixed anchor 603 and fitting it into a suture holding cavity 206 (FIG. 25). The rectangular rear 205 (FIG. 25) of the sliding pin 203 drops into the rear pin slot 211 shown in FIG. 26, allowing the suture unit stretcher 202 (FIG. 24) to pull on the looped end 605 of the suture unit so that the material is held taut. The needle 401 catches the taut thread at its hooked end 403 as it moves toward the receiver arm 002. The suture unit 601 slides off the suture stretcher and moves toward the fastener 501 (FIG. 28) with the needle 401.

Figures 30, 31:
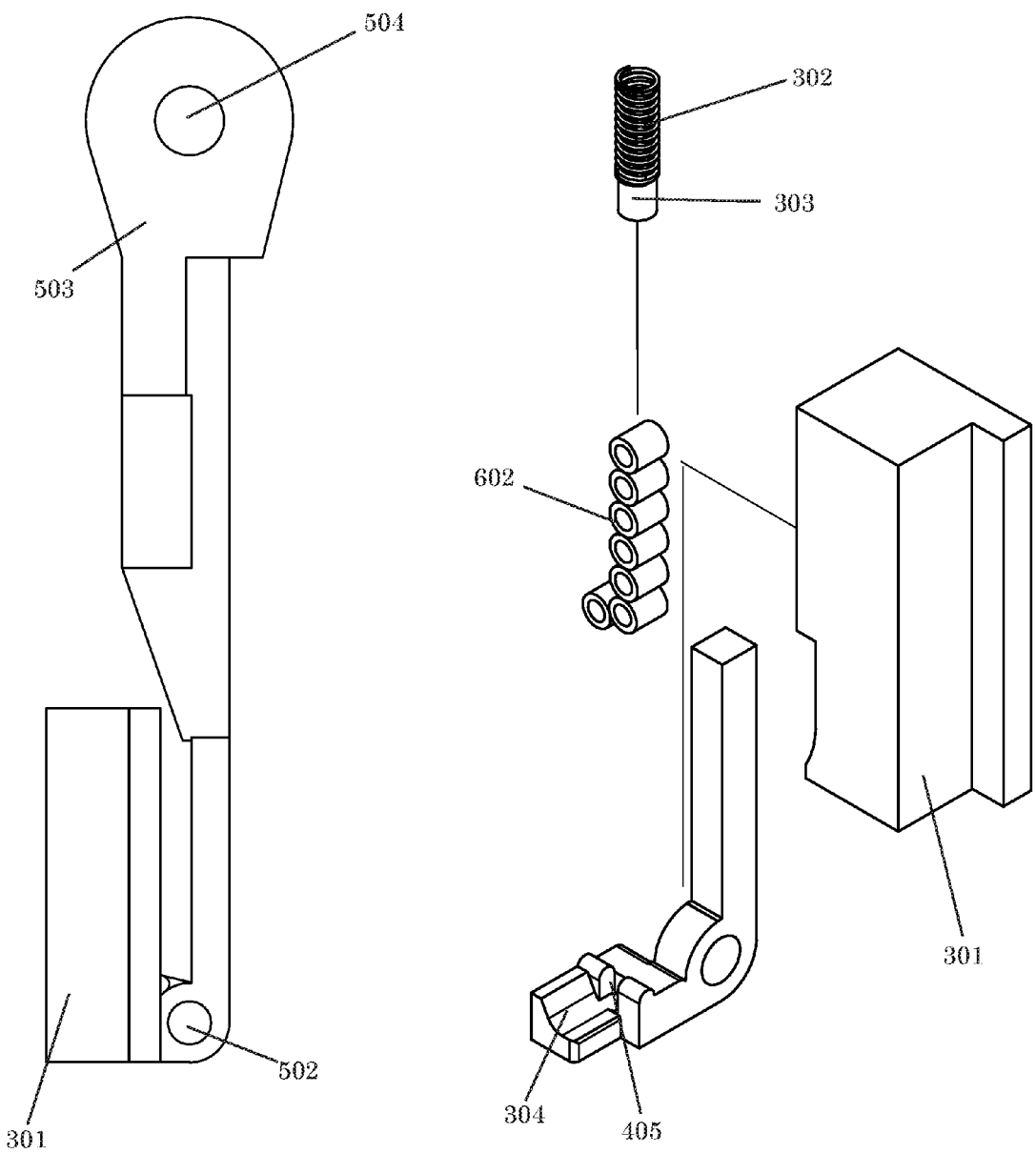
FIG. 30 illustrates the side view of the fastening mechanism of the first embodiment.
FIG. 31 illustrates the exploded view of the fastening mechanism of the first embodiment.

With continued squeezing of arms 001 and 002, the threaded needle penetrates through the everted edges of tissue and emerges with the suture unit 601 still attached in the hooked end 403. The fastener 501 secures the looped end 605 of the suture material with a secondary fastened anchor 603. As the threaded needle 601 reaches the receiver arm 002, it enters a needle passageway 405 that directs the needle to enter a crimped anchor 602 that is waiting at the crimped anchor holder 304 (FIG. 31). By crimped anchor, we mean the anchor that will be crimped or secured over the suture thread after the needle has pierced the skin. Once the device has reached its maximum compression, the user relaxes his/her grip on the device. The torsion spring 006 reverts the device's arms back to their initial positions as shown in FIG. 1. This spring force powers the fastening of the crimped anchor 602.

Figure 29:
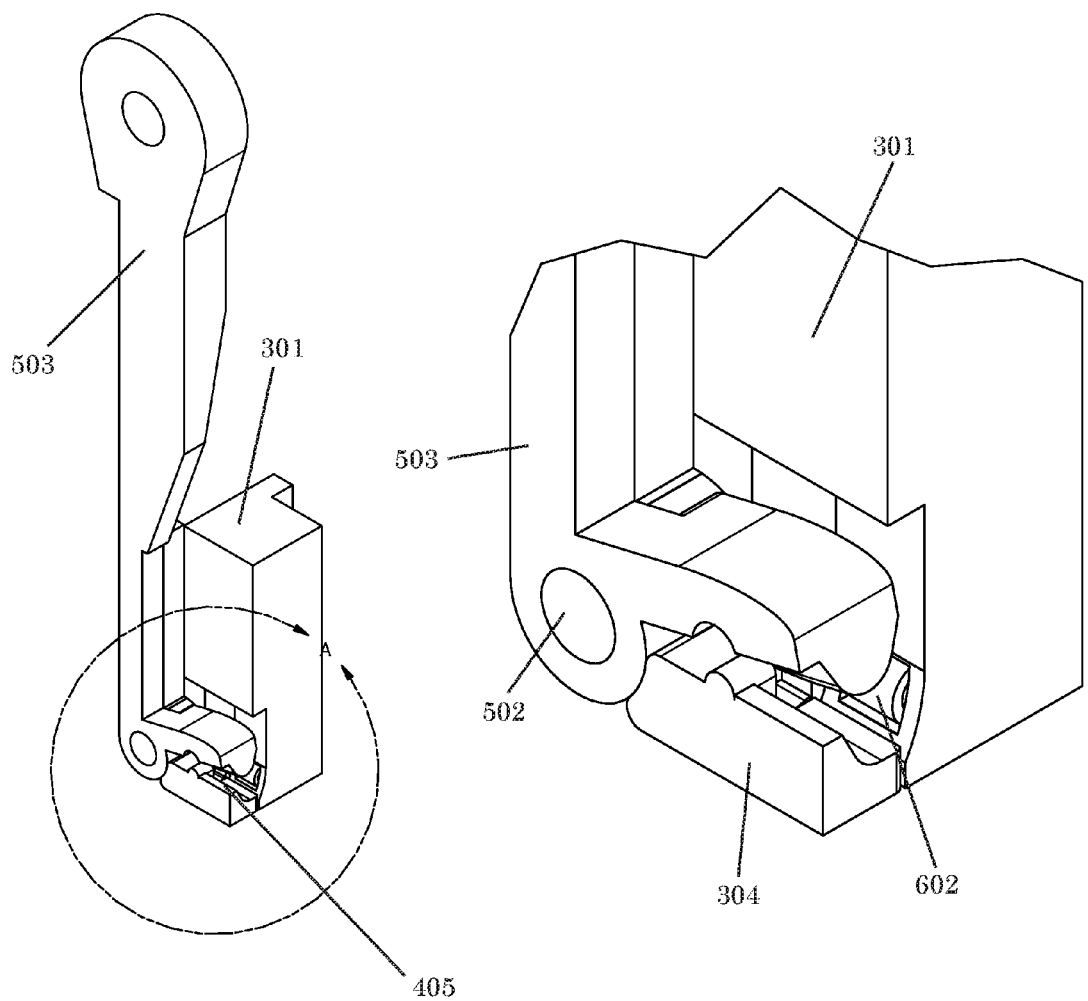
FIG. 29 illustrates the close-up auxiliary view of the fastening mechanism of the first embodiment.

The pulling away of the middle arm 003 and the driver arm 001 pulls at the linkage arm 013 (FIG. 9), which causes the fastening lever 503 to rotate around the lever axle 504 (FIG. 30), pushing down on the crimped anchor 602 and fastening the crimped anchor against the crimped anchor holder 304 (FIG. 29). The fastening lever 503 is affixed to the receiver arm 002 by a fastening axle 502 (FIG. 29), about which the fastening lever is free to rotate. The entire fastener 501 mechanism is housed in the fastening chamber 505 (FIG. 15), located near the distal end 011 of the receiver arm 002. The linkage arm 013 rotates about the lever axle 504 and the linkage arm hinge pin 016 (FIG. 6) located inside the driver arm 001.

Figure 28:
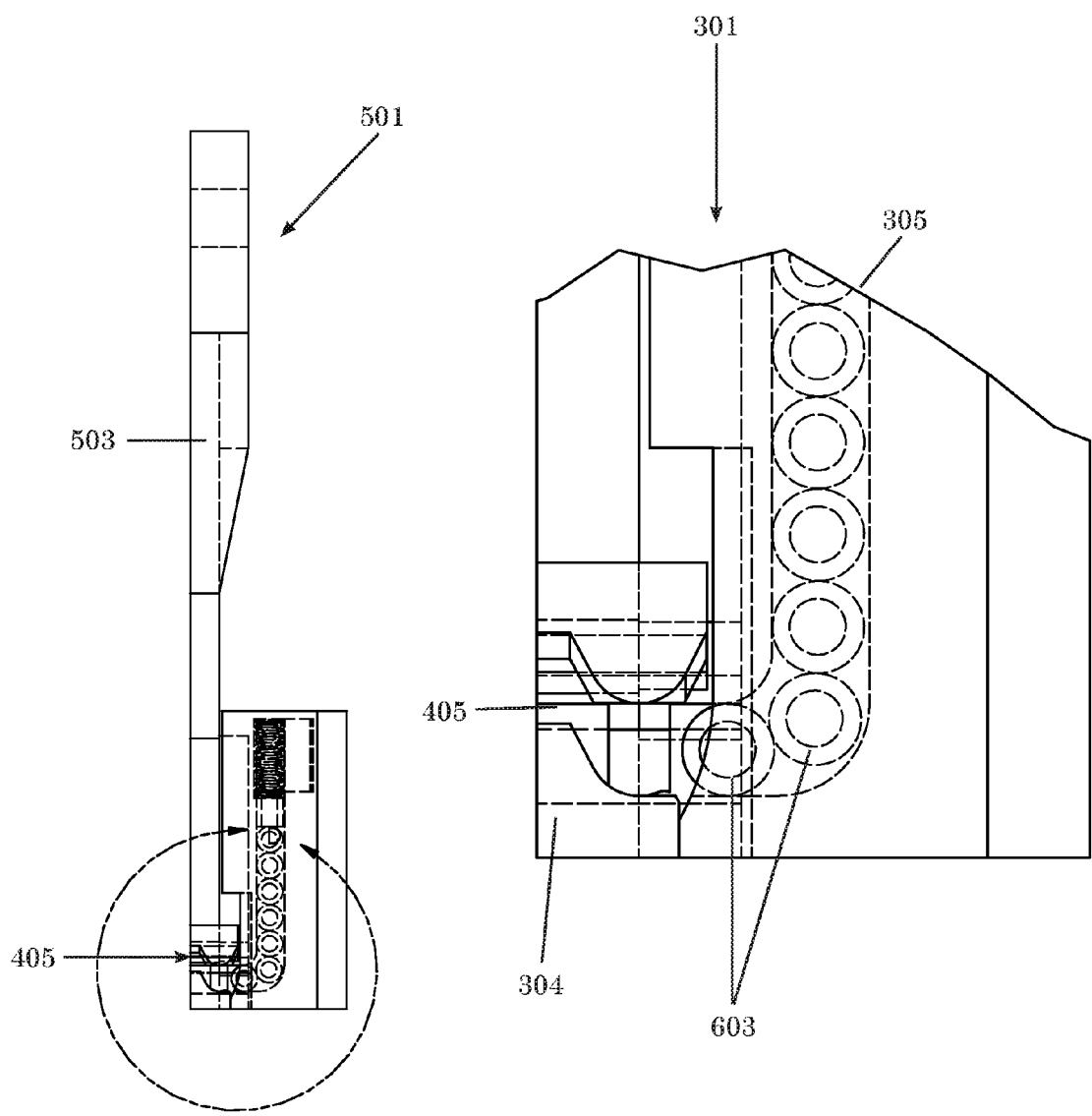
FIG. 28 illustrates the close-up view of the crimped anchor-loading mechanism of the first embodiment.
Figure 32:
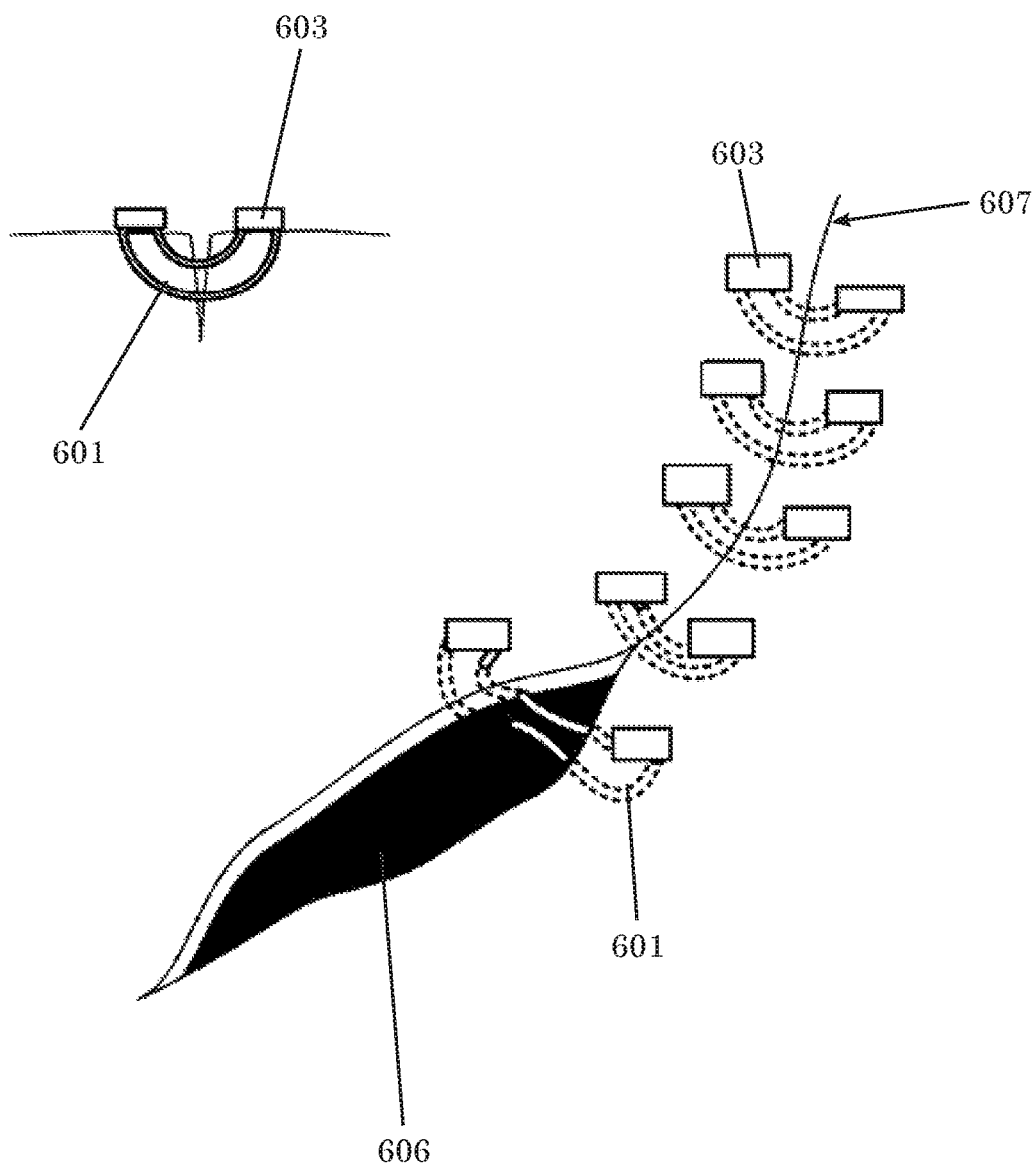
FIG. 32 illustrates the expected result of using the first embodiment to suture a wound.

Crimped anchors 602 are stacked in a loading channel 305 of FIG. 28 running through a loading house 301 and are released into the crimped anchor holder 304 as the user removes a fastened crimped anchor from the crimped anchor holder 304 following a single squeeze of the arms of the device. As the fastened crimped anchor 603 is released from the crimped anchor holder 304, a loading spring 302 (FIG. 31) exerts a force on the anchor feeder 303, which pushes the next crimped anchor 602 into the crimped anchor holder 304 in preparation for the next suture as shown in FIG. 11. FIG. 32 illustrates the expected result of using the first embodiment to suture a wound where 606 represents an open wound, 607 represents a wound closed with a suture device of the first embodiment (FIG. 1).

Figure 33:
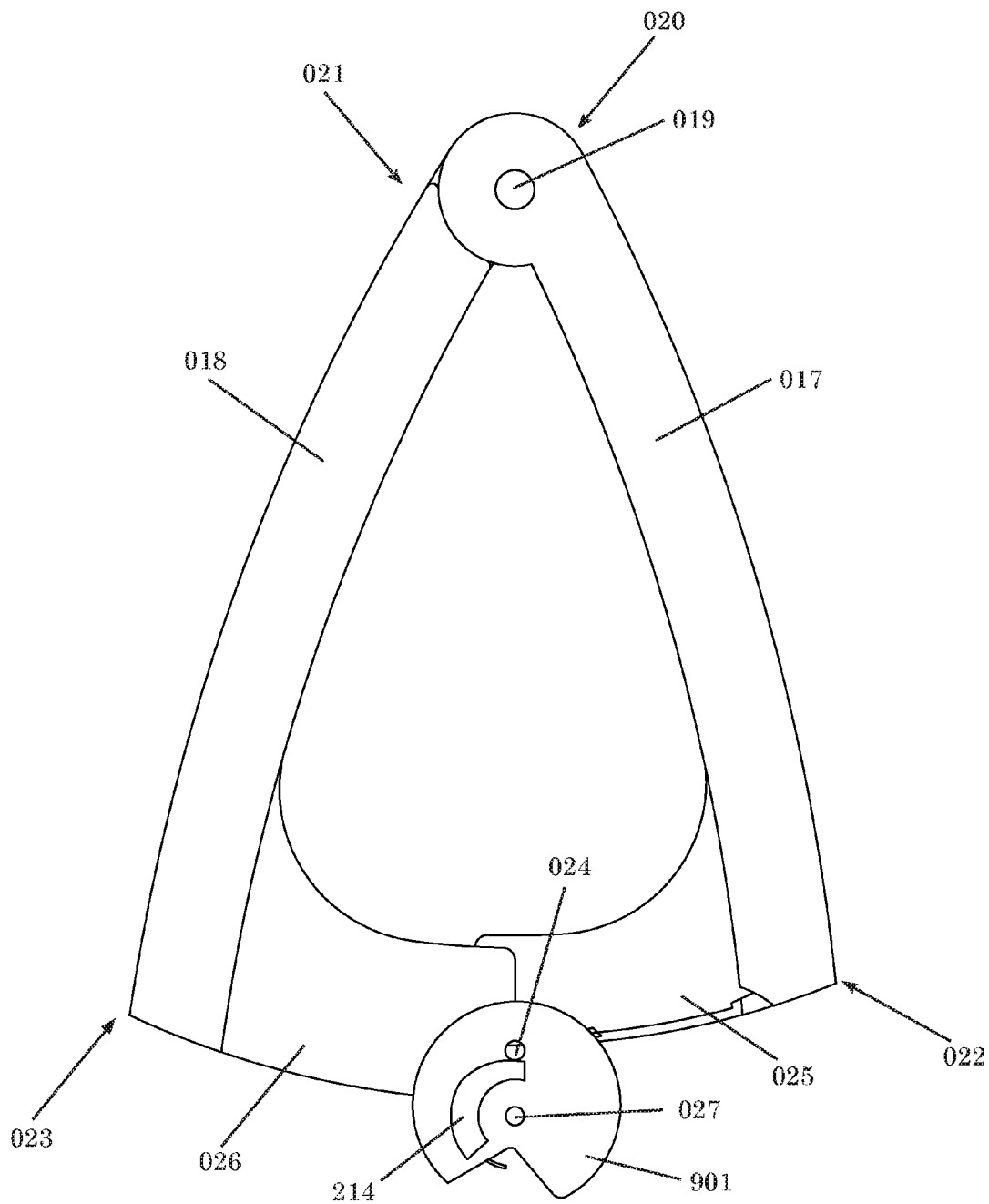
FIG. 33 illustrates the frontal view of the second embodiment in its open configuration.
Figure 34:
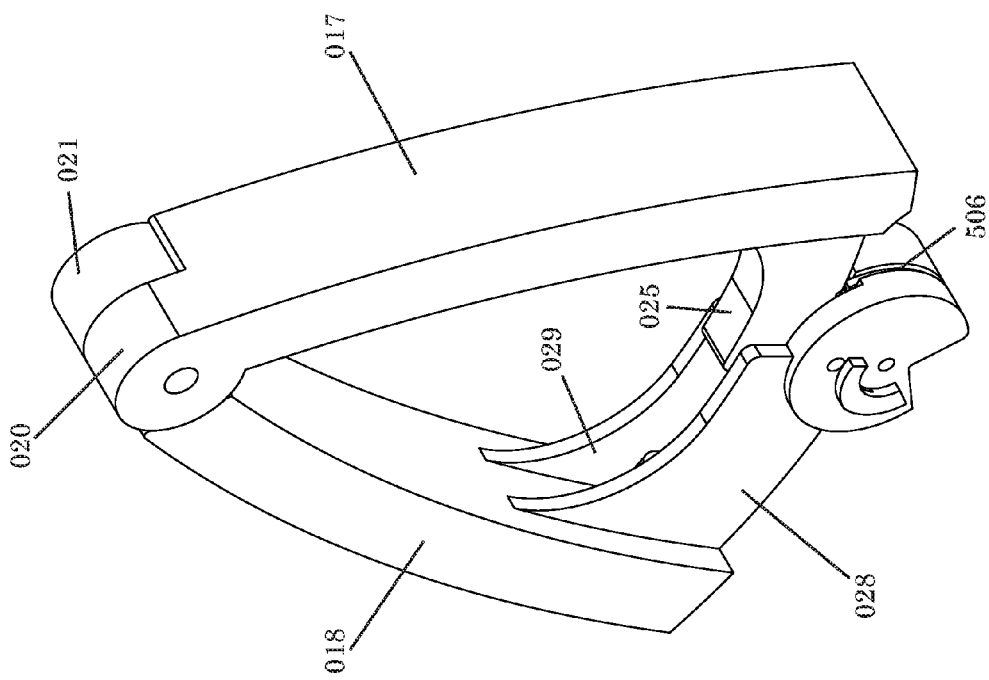
FIG. 34 illustrates the top auxiliary view of the second embodiment in its open configuration.
Figure 36:
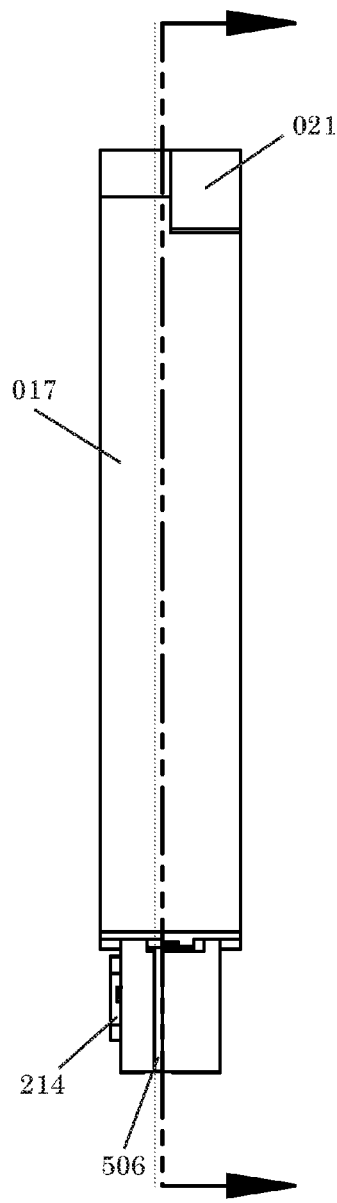
FIG. 36 illustrates the side view of the second embodiment in its closed configuration.

A second embodiment of the invention is shown in FIGS. 33-69. Both the driver arm 017 and the receiver arm 018 of FIG. 33 can be, in part or in whole, straight, curved, articulated, branched, or otherwise composed of multiple segments. This ensures that the suturing device of FIG. 34 can be held comfortably in one hand and operated with one hand.

Figure 35:
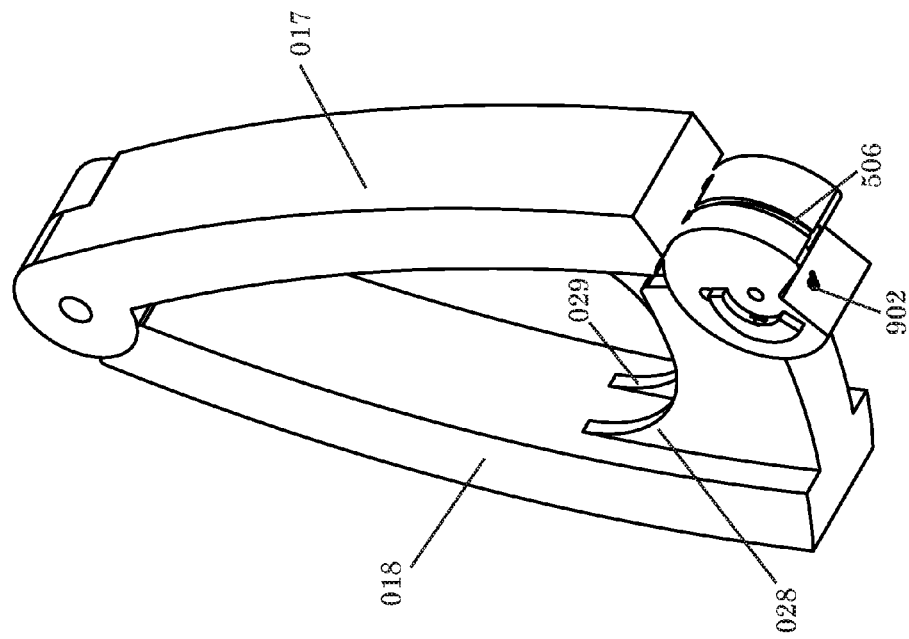
FIG. 35 illustrates the bottom auxiliary view of the second embodiment in its closed configuration.

In FIG. 35 the distal end 022 of the driver arm 017 and the distal end 023 of the receiver arm 018 are in communication with the center assembly 901. As seen in FIG. 1, the proximal end 020 of the driver arm 017 and the proximal end 021 of the receiver arm 018 are connected at a hinge 019. The distal end 023 of the receiver arm 018 extends into a pair of receiver limbs 026, comprising of a front receiver limb 028 and a rear receiver limb 029.

Figure 37:
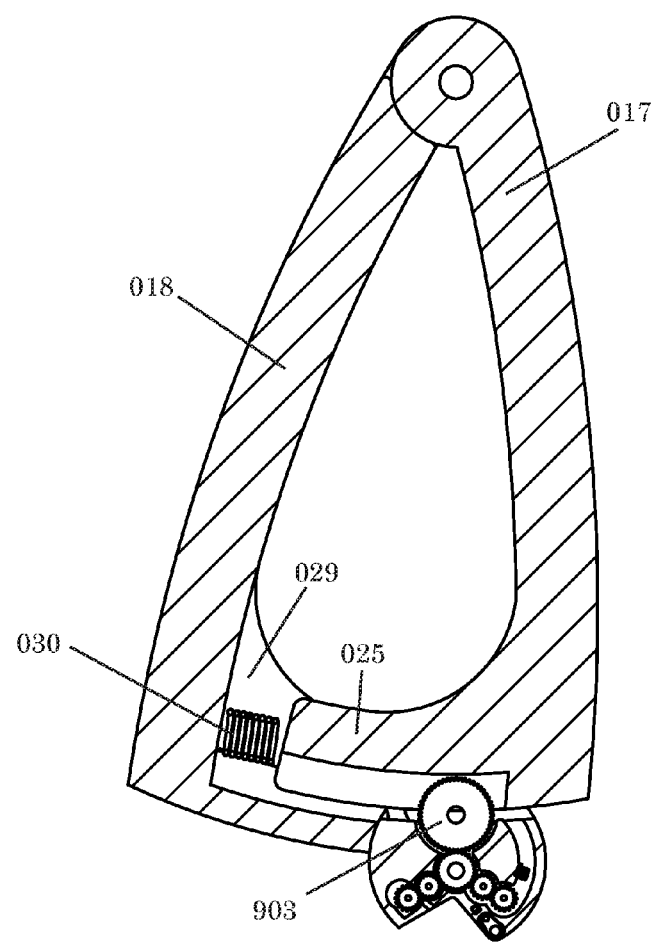
FIG. 37 illustrates the cross-sectional view of the second embodiment in its closed configuration.

Between the front receiver limb 028 and the rear receiver limb 029 lies a retraction spring 030 that is irreversibly attached to the distal end 023 of the receiver arm 018 by a strong adhesive or anchor (FIG. 37). The retraction spring 030 is in communication with the driver limb 025 extending from the distal end 022 of the driver arm 017. The retraction spring 030 resists the squeezing of arms 017 and 018 until a physical contact point is reached. After this point, the device automatically impels a number of functions that proceed to completion, much like a commercial stapler.

Figure 39:
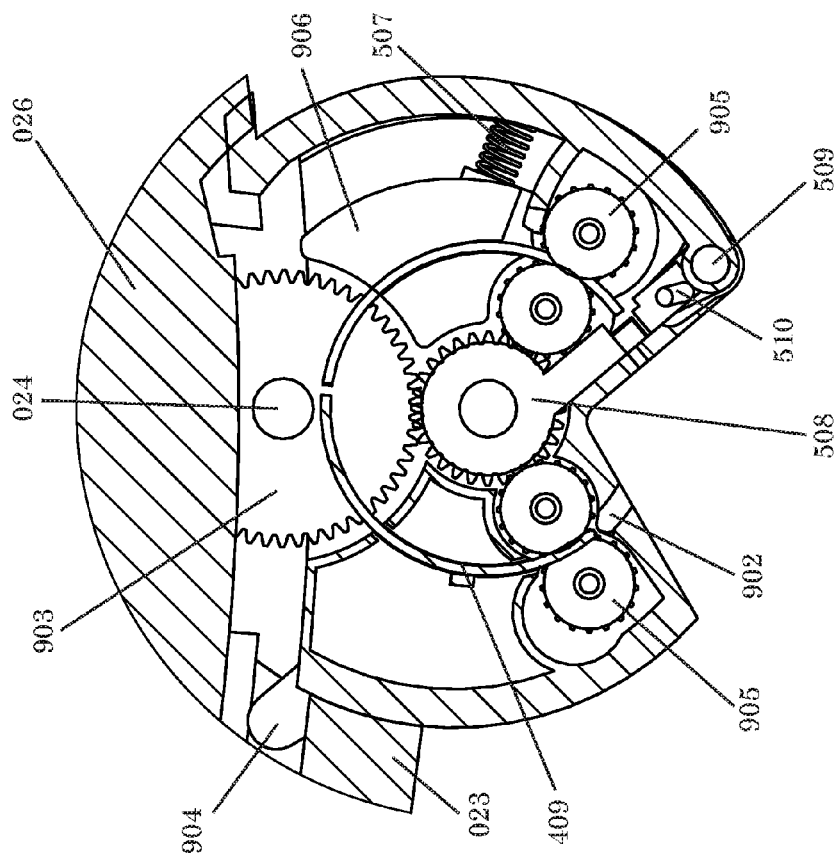
FIG. 39 illustrates a magnified view of the center assembly of the second embodiment.
Figure 38:
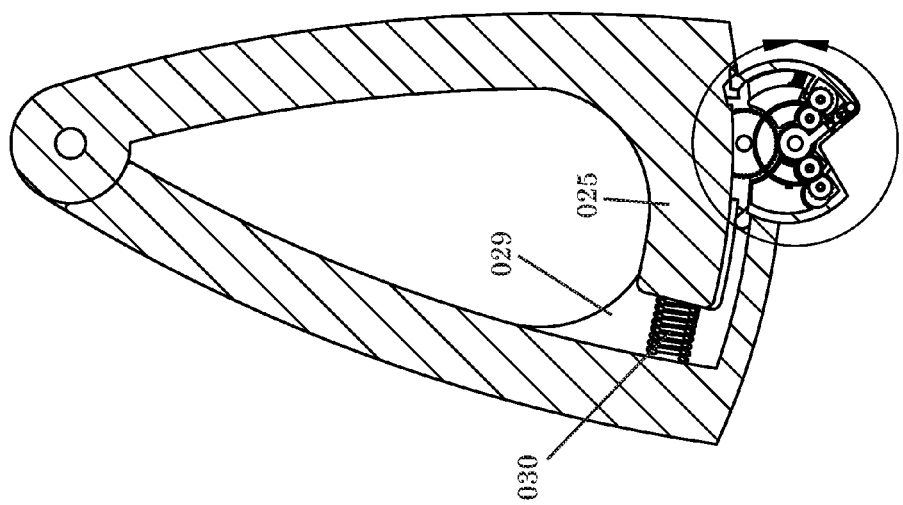
FIG. 38 illustrates the cross-sectional view of the second embodiment in its closed configuration with attention to the center assembly.
Figure 41:
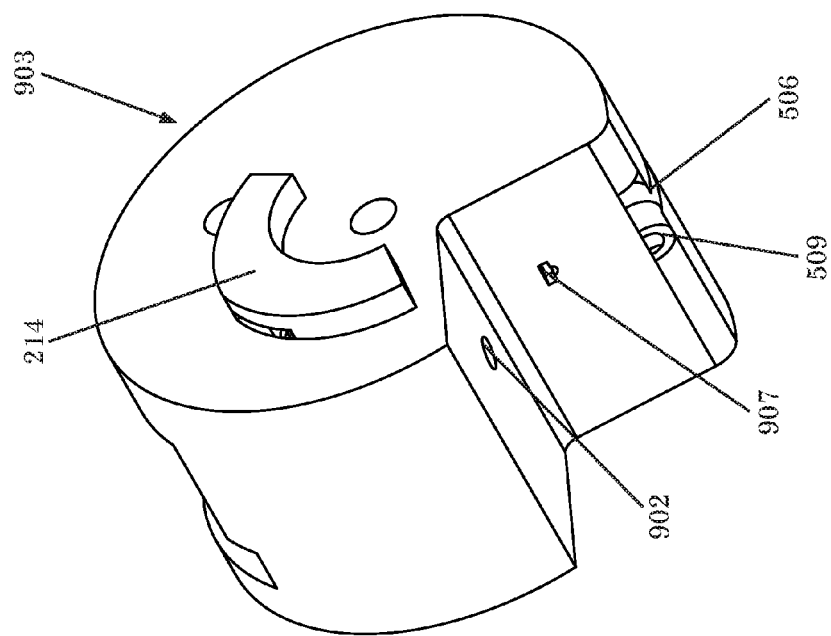
FIG. 41 illustrates the bottom auxiliary view of the center assembly of the second embodiment.
Figure 40:
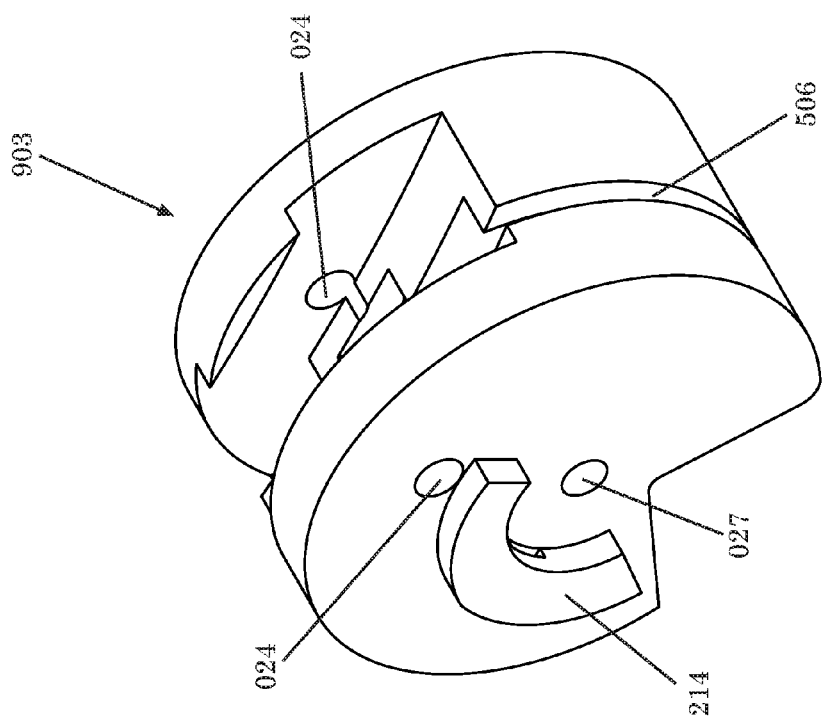
FIG. 40 illustrates the top auxiliary view of the center assembly of the second embodiment.
Figure 42:
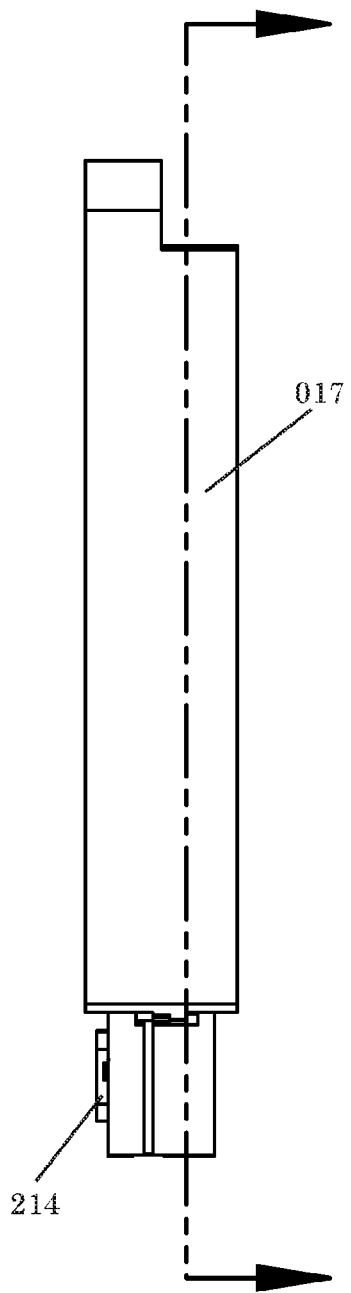
FIG. 42 illustrates the side view of the driver arm of the second embodiment.
Figure 43:
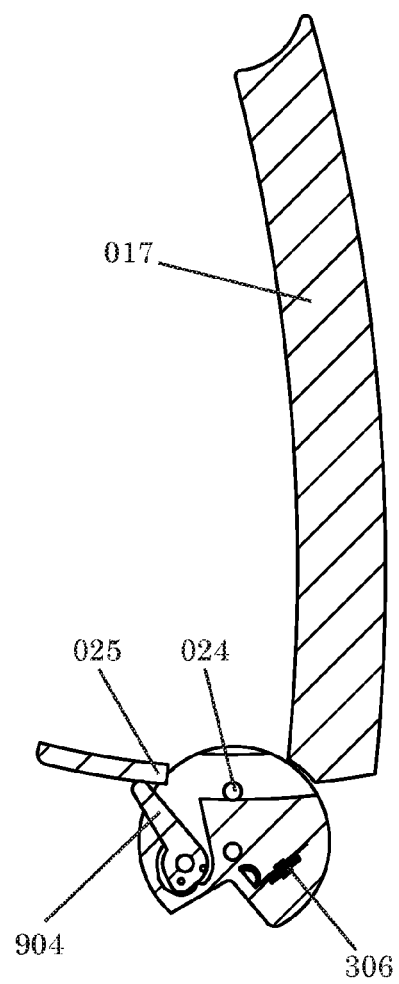
FIG. 43 illustrates the cross-sectional view of the gear actuation mechanism of the second embodiment.
Figure 44:
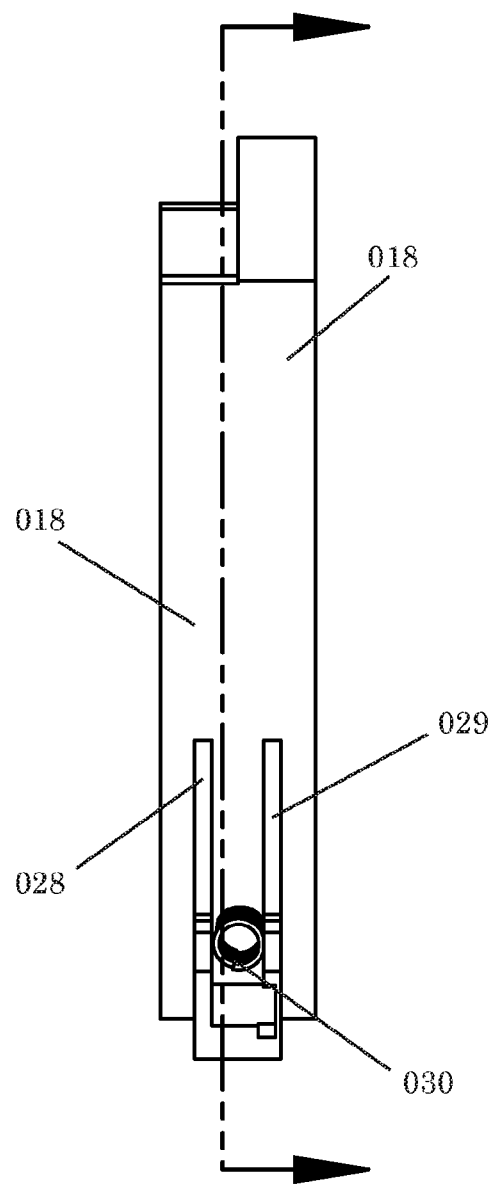
FIG. 44 illustrates the side view of the receiver arm of the second embodiment.
Figure 45:
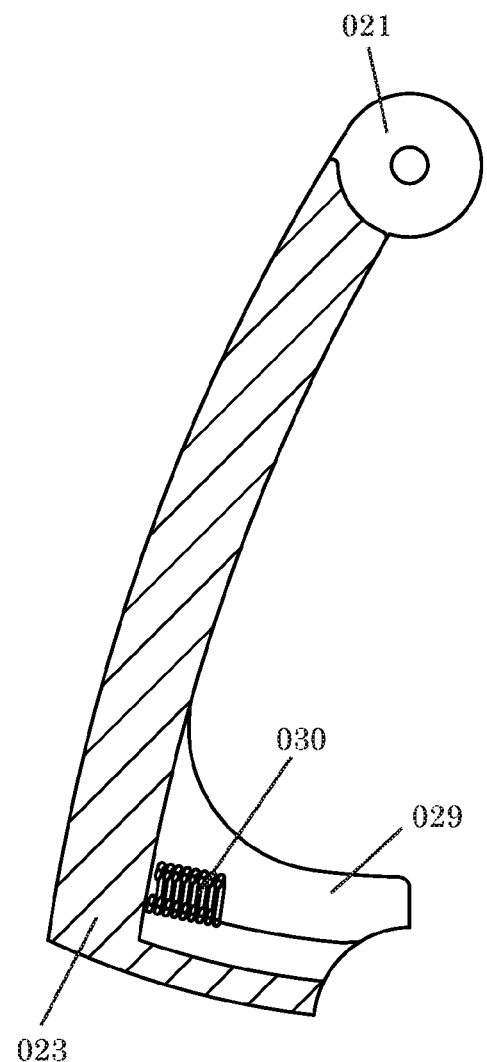
FIG. 45 illustrates the cross-sectional view of the driver arm of the second embodiment in its closed configuration.
Figure 47:
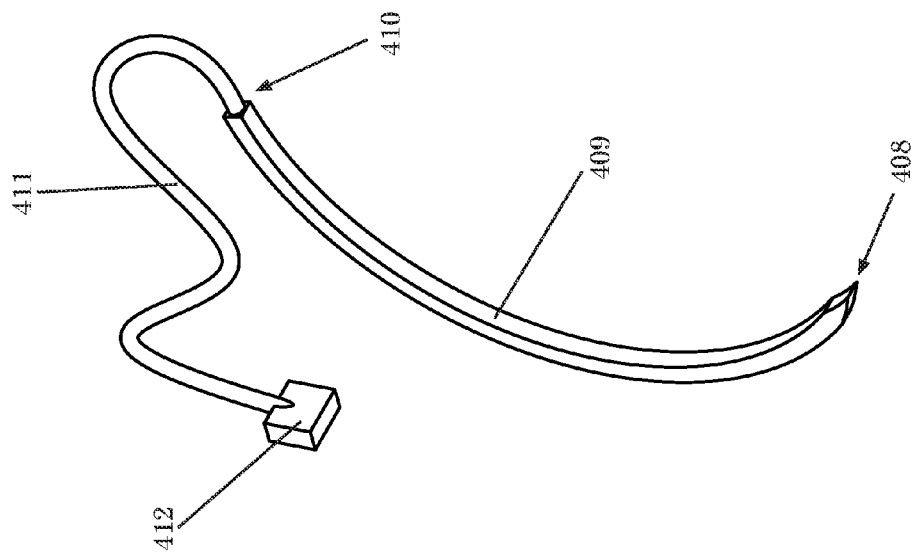
FIG. 47 illustrates the top auxiliary view of the freed suture unit of the second embodiment.
Figure 46:
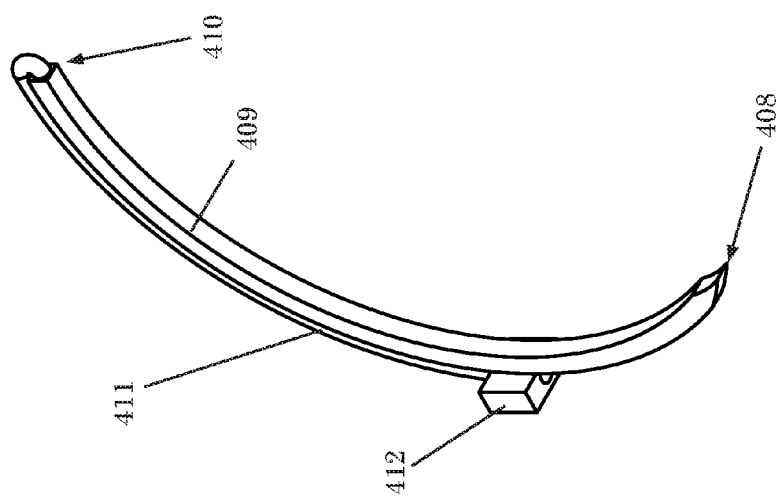
FIG. 46 illustrates the top auxiliary view of the loaded suture unit of the second embodiment.
Figure 49:
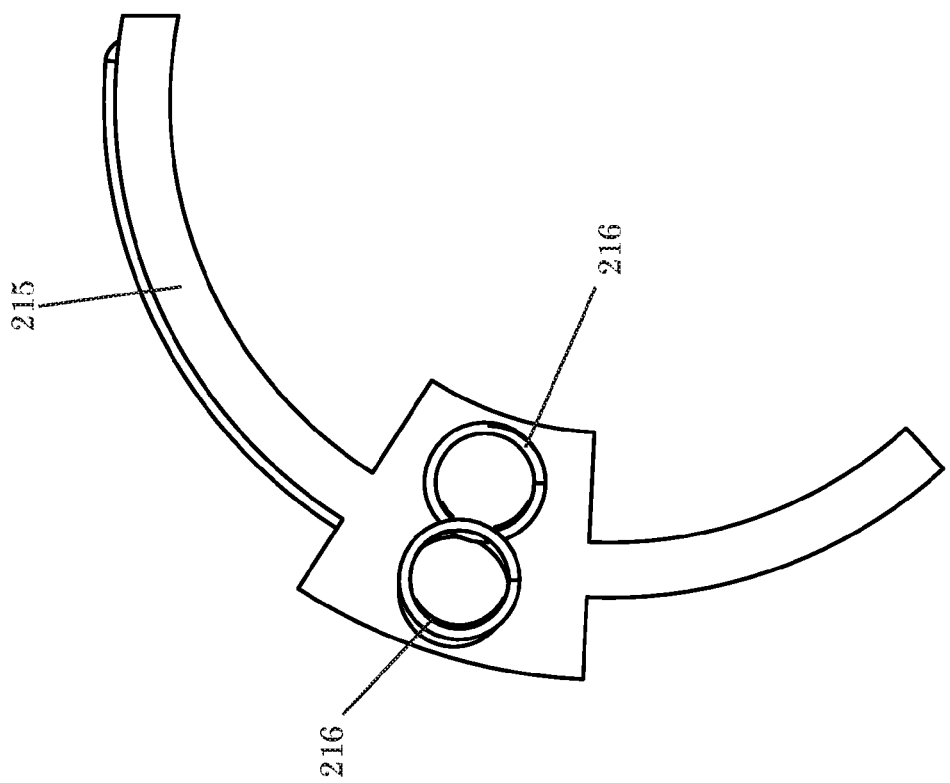
FIG. 49 illustrates the frontal view of the suture unit loading mechanism of the second embodiment.
Figure 48:
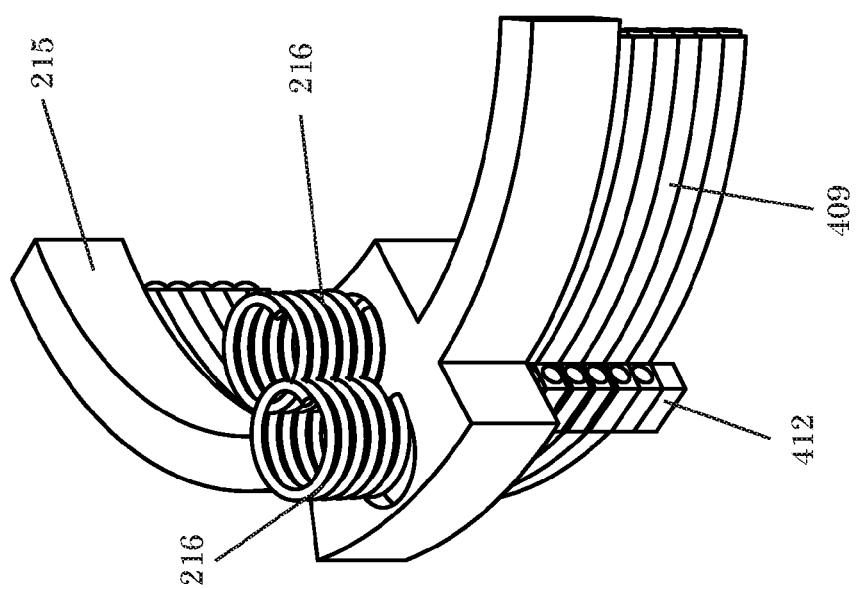
FIG. 48 illustrates the top auxiliary view of the suture unit loading mechanism of the second embodiment.
Figure 52:
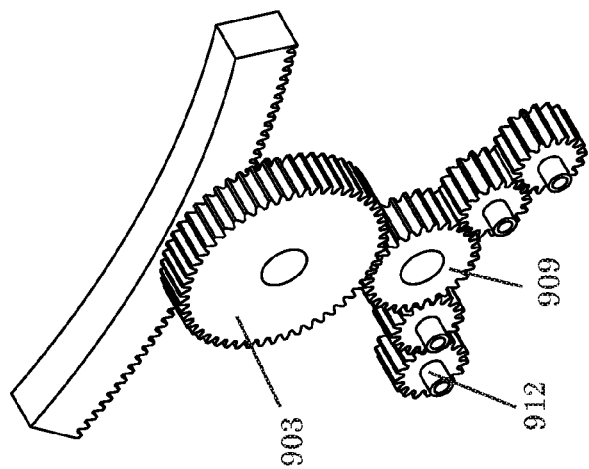
FIGS. 50, 51, and 52 illustrate the frontal and auxiliary views of the gear train of the second embodiment.
Figure 68:
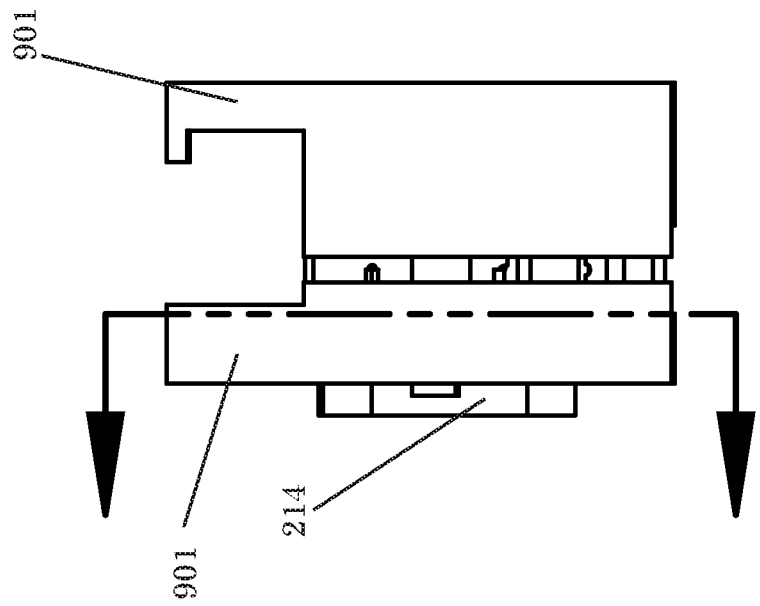
FIG. 68 illustrates the side view of the center assembly of the second embodiment.

Upon squeezing of arms 017 and 018, a gear actuating lever 904 is pushed (FIG. 43), moving a connected pinion 911 and its bore 912 through the gear actuation slot 917 (FIG. 68). The O-ring 905 surrounding the actuating pinion bore 912 moves toward another O-ring 905, trapping the shaft 409 of a needle housed in the needle loading cavity 214 (FIG. 39). Once the needle is trapped, the gear rail 908 in FIG. 50 on the driver arm 017 interacts with the compound gear 903, initiating the piercing of the needle into tissue. The needle 409 is attached to the proximal end of a length of suture material 411 through the needle swage 410 (FIG. 47). The distal end of the suture material 411 comprises a preformed fixed anchor 412. The needle 409, the suture material 411, and the fixed anchor 412, form the suture unit. One or more suture units are contained in the needle loading cavity 214, in which the needles are pushed by the needle driving part 215 by a needle loading spring 216 (FIG. 48).

Figure 51:
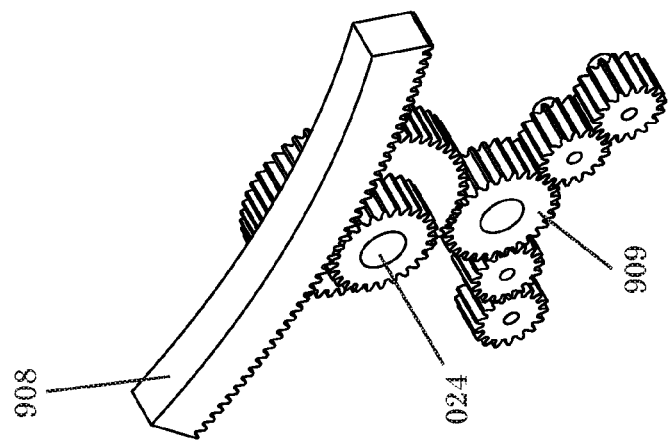
Figure 50:
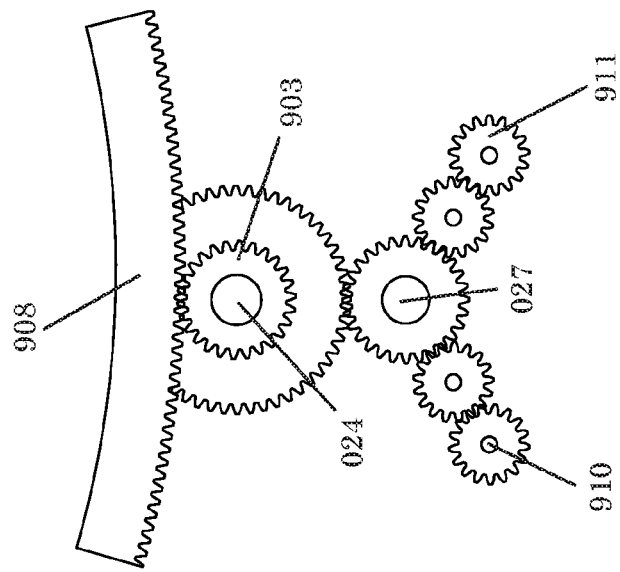
Figure 53:
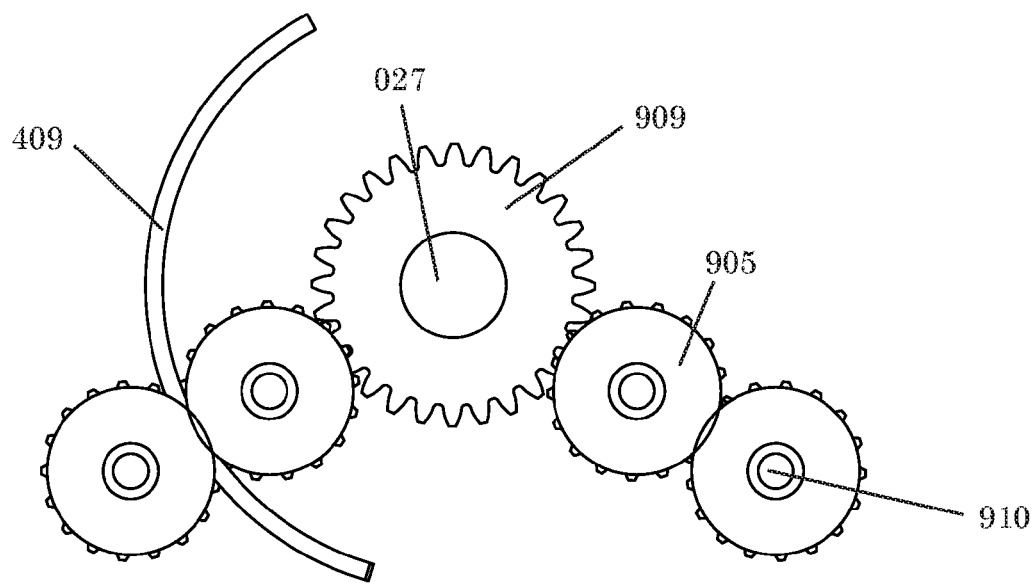
FIG. 53 illustrates the frontal view of the friction drive of the second embodiment.
Figure 54:
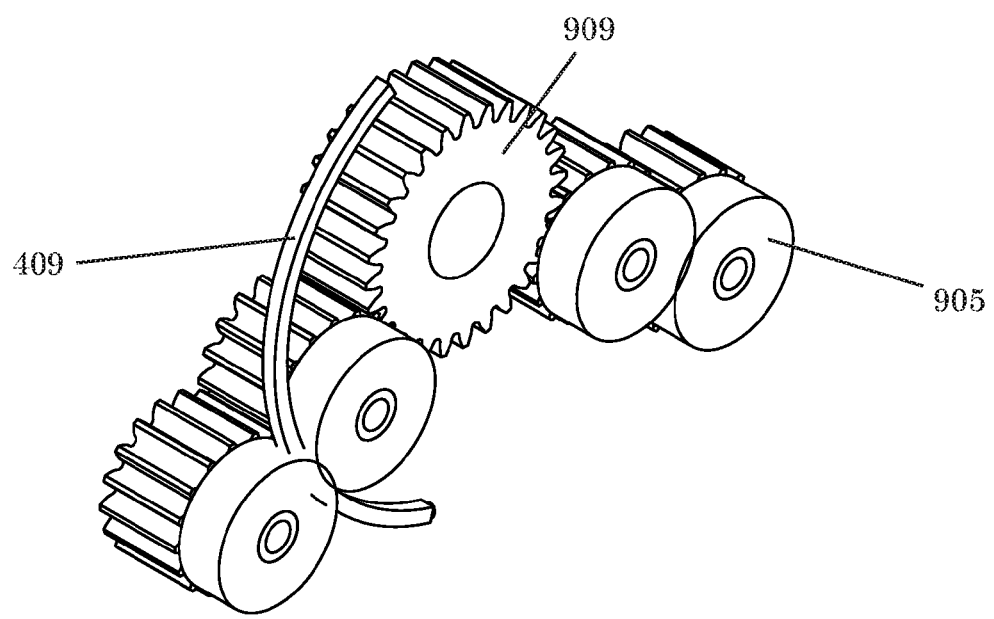
FIG. 54 illustrates the auxiliary view of the friction drive of the second embodiment.
Figure 57:
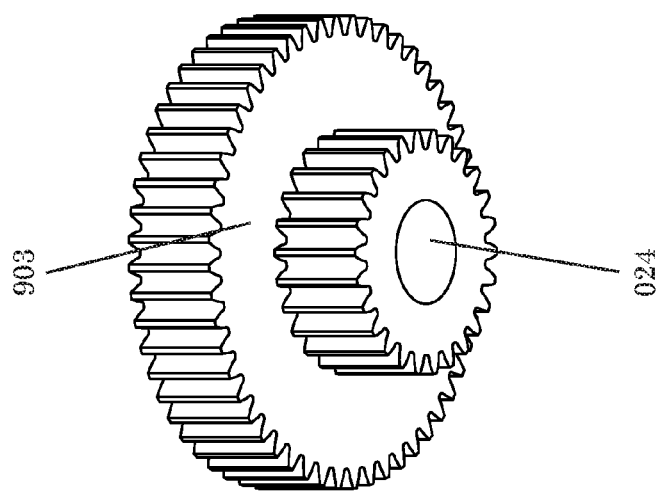
FIGS. 55, 56, and 57 illustrate the side, front, and auxiliary views, respectively, of the compound gear of the second embodiment.
Figure 56:
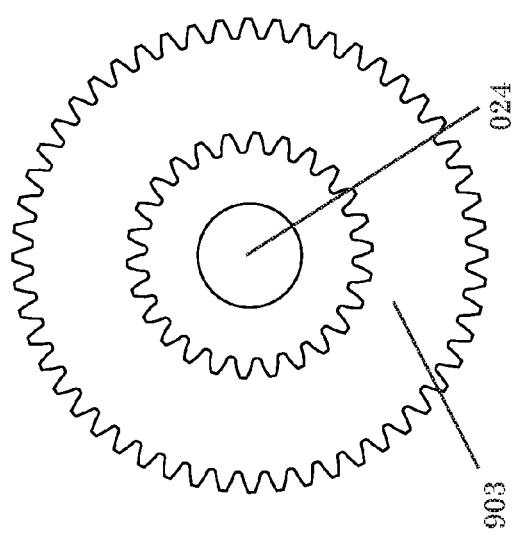
Figure 55:
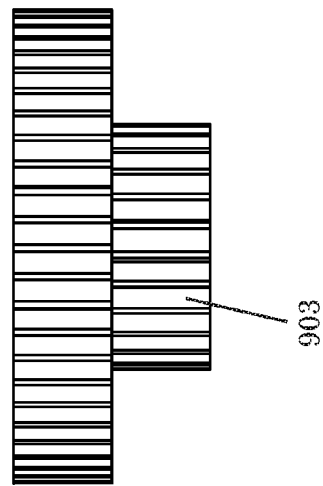
Figure 62:
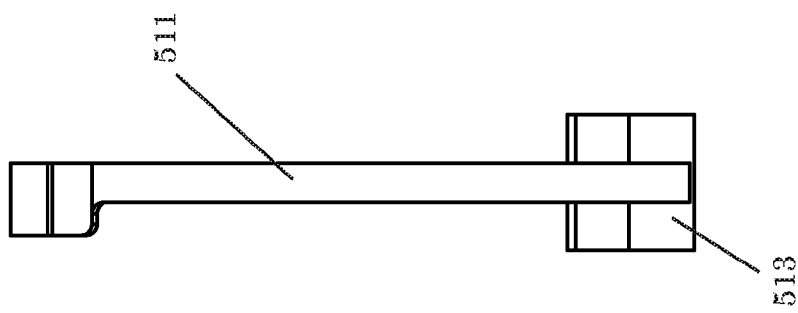
FIGS. 60, 61, and 62 illustrate the front, side, and back views, respectively, of the crimped anchor fastening mechanism of the second embodiment.

The compound gear 903 rotates in a counterclockwise direction about the compound gear clearance 024, pushing a center gear 909 to rotate clockwise about the center gear clearance 027 (FIG. 51). The center gear 909 rotates two pairs of pinions 911, one pair on either side of the center gear 909, about their respective pinion clearances 910. The O-rings 905 rotating with the pinion bores 912 direct the needle into a circular counterclockwise path out of the center assembly 901 (FIG. 54). Upon exiting the center assembly through the needle exit clearance 902, the needle point 408 enters the tissue, continues to move through the edges of the wound in a circular fashion while dragging the attached suture material along with it.

Figure 61:
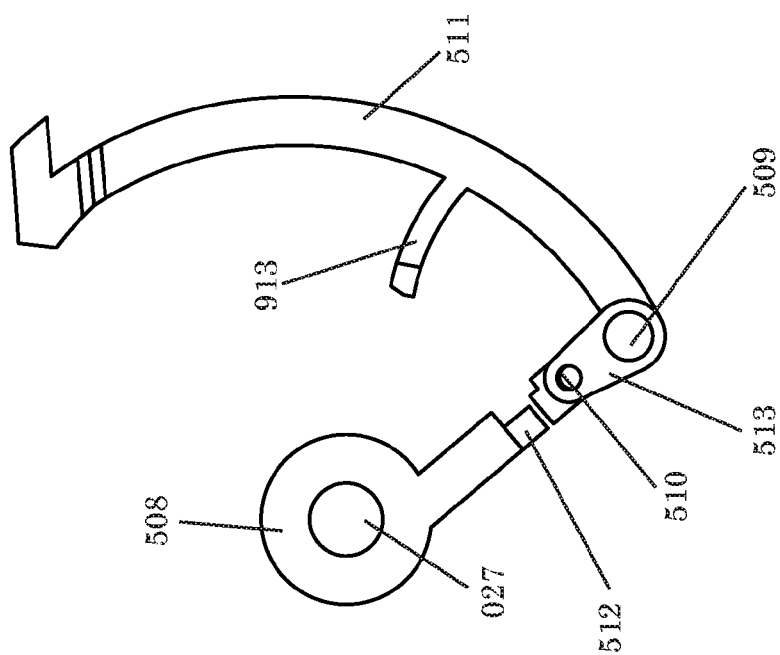
Figure 60:
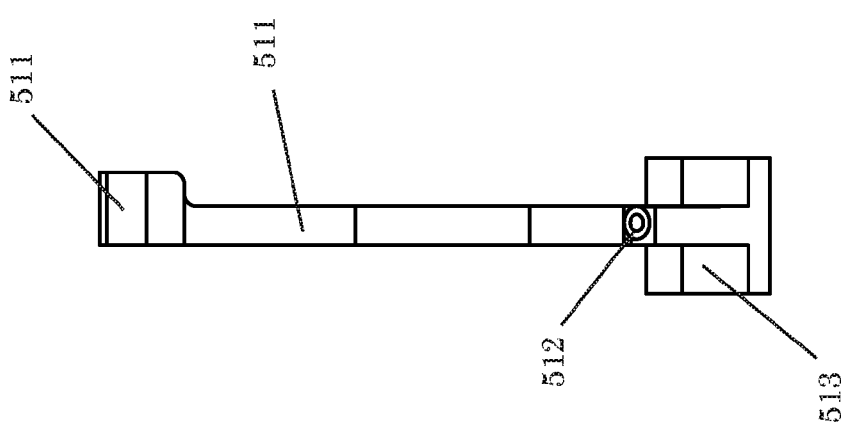
Figure 63:
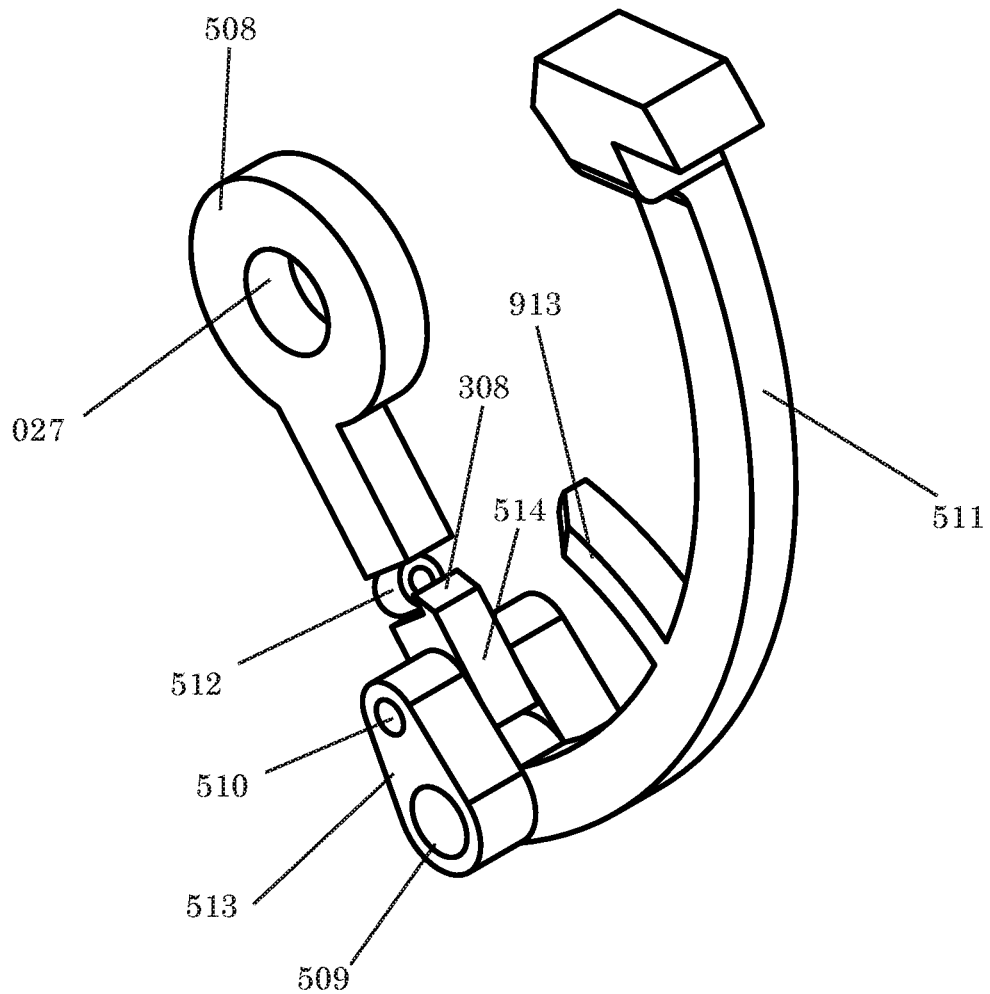
FIG. 63 illustrates the top auxiliary view of the crimped anchor loading mechanism of the second embodiment.
Figure 66:
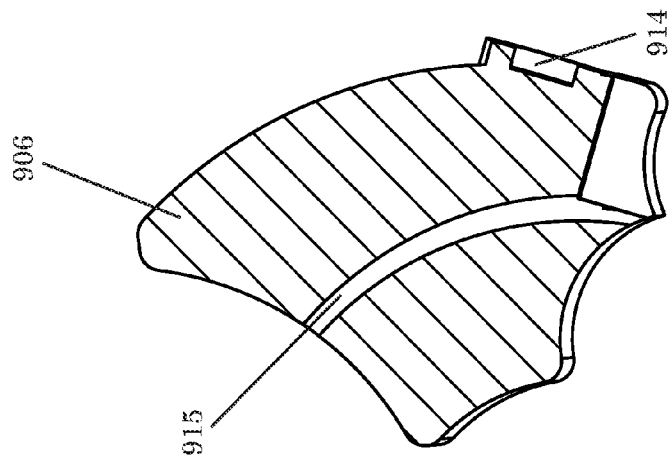
FIGS. 64, 65, and 66 illustrate the bottom auxiliary, top auxiliary, and side views, respectively, of the needle expulsion platform of the second embodiment.
Figure 65:
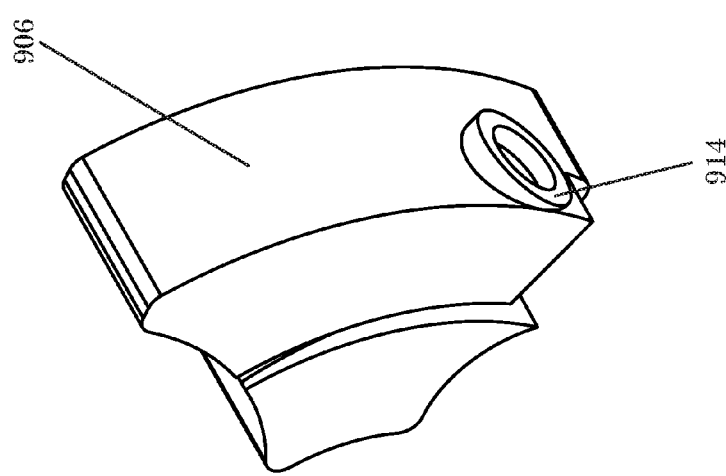
Figure 64:
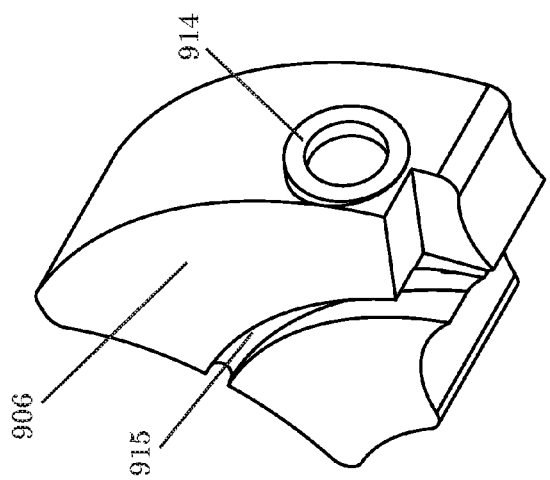
Figure 67:
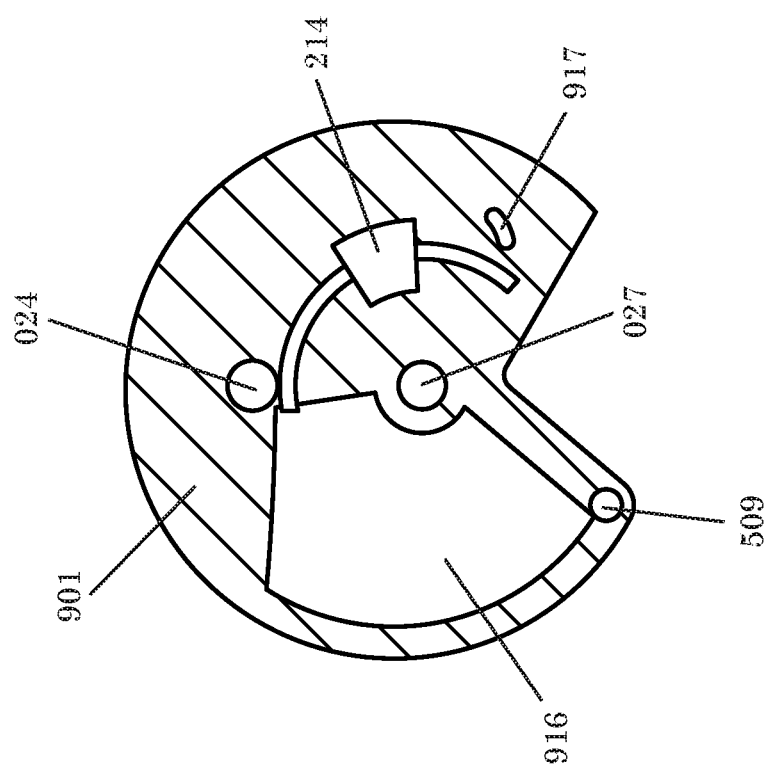
FIG. 67 illustrates the cross-sectional view of the needle expulsion cavity of the second embodiment.

Once the needle 409 reaches the center assembly 901, the needle enters the needle entrance clearance 907 and continues into the crimped anchor 512 located in the crimped anchor loading channel 306 in between the fastening barrier 508 and the fastener 514 (FIG. 61). The fixed anchor does not enter the tissue, and as such, the proximal end of the suture material 411 meets a blade 308 that disjoints the needle from the suture material (FIG. 61). As the disjointed needle 409 continues on its circular path through the crimped anchor 512, the needle 409 meets the second pair of O-rings 905 attached to the pinion bores 912. The O-rings 905 direct the needle 409 onto the needle expulsion platform 906, where the needle is directed off the plane of the circular needle path through the needle elevating cavity 915 (FIG. 67).

As the driver arm 017 reaches maximum compression of the retraction spring 030, the distal end of the driver 023 actuates the fastener trigger 511, rotating the fastening lever 513 about the fastening pivot 509 (FIG. 61). The fastening pivot 509 moves the fastening pinhole 510 to actuate the fastener 514, which fastens the crimped anchor 512 onto the proximal end of the suture material 411. The needle remover 913 also rotates with the fastening lever 513 to release the needle from the grip of the O-rings 905 and expel the needle into the needle disposal cavity 916 (FIG. 67). The needle disposal system comprises the needle remover 913, the fastening lever 513, the needle expulsion platform 906, and the needle disposal cavity 916. The user's grip on the device's arm is then relaxed and the arms return to their initial open configuration. While the arms return to their initial open configuration, the fastened crimped anchor 512 exits the center assembly 901 through the needle entrance clearance 907. Another crimped anchor 512 is then prepared for the next suture unit in the crimped anchor loading channel 306, through which a series of crimped anchors are pushed along with a crimped anchor pin 309 under the influence of a constant force spring 307 (FIG. 59). The fastening trigger 511 returns to its original position from the force of a biasing spring 507 located in the biasing spring house 914. FIG. 69 illustrates the expected result of using the second embodiment to suture a wound wherein 606 represents an open wound, 607 represents a wound closed with a suture device of the first embodiment (FIG. 33) and 608 is a suture unit.

To use the present invention, the user first approximates the edges of the wound with forceps, everting the edges of tissue to the desired length. The user then places the device in its open configuration over the everted tissue, ensuring that the tissue interferes with the needle's projected path and that the lowest point of the device is against the tissue. When ready to suture, the user squeezes both arms of the device to maximum compression. After attaining maximum compression, the user gently releases his grip on the device, allowing the arms of the device to return to their open positions. The user then lifts the device and forceps off the tissue and allows the tissue edges to relax. In some embodiments, it may be necessary for the user to load a cartridge of suture units before approximating the edges of the wound.

Optionally, the present invention may be used in conjunction with one or more of the following: antibiotics to prevent bacterial wound infection, anesthetic to ease the painful process, and antiseptic to cleanse the wound prior to suturing.

In one embodiment, the suturing device of the invention comprises metal components and preferably metals appropriate for surgical devices, such as stainless steel or tungsten or alloy thereof.

In another embodiment, the suturing device of the invention comprises extruded, molded, or machined thermoplastic material(s) that are known to be biocompatible with surgical applications. The suitable thermoplastic materials include, but are not limited to, poly-acrylates and methacrylates, polyolefins, ethylene-propylene copolymers; SE/BS, polycarbonates, fluorocarbon polymers, poly-tetrafluoroethylene, polysiloxanes, polyperfluoroethylene-propylene, various aliphatic and aromatic polymers or block copolymers, polyvinylchloride polymers, various polyesters including dacron or polyethylene terephthalate or combinations thereof.

In another embodiment, the suturing device of the invention comprises a high-strength technical ceramic as ceramic materials are lightweight, of high strength and are non-allergenic. Embodiments intended for repeated use must be sterilized between uses, so materials that will tolerate sterilizing agents, solvents, or autoclave temperatures are preferred.

The disclosure in this application is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded with the widest scope encompassing numerous alternatives and modifications consistent with the principles and features disclosed. For purpose of clarity, details relating to technical material that is known in the technical fields related to the invention have not be described in detail so as not to unnecessarily obscure the present invention. For example, the device may employ any type of anchor of any material that is durable and securely holds suture material. Similarly, the device as well as any of its components can be scaled to accommodate wounds of different mammalian tissue as well as suture material of varying thickness.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

We claim:

1. A suturing device comprising:
   a. a driver arm and receiver arm, each comprising a distal end and a proximal end, said driver and receiver arms connected by a hinge at their proximal ends, said hinge being configured to allow said distal ends of said driver arm and said receiver arm to converge and separate through rotation about said hinge while keeping said proximal ends of both arms affixed to each other;
   b. one or more suture units capable of securing wound tissue housed in a crimped anchor loading system, said suture units comprising a length of suture material having a proximal end and a distal end, a fixed anchor attached to said proximal end of the suture, and a needle attached to the distal end of the suture;
   c. a center assembly attached to the distal end of the receiver arm and in communication with the driver arm, said center assembly comprising, a suture unit loading system, the crimped anchor loading system, a crimped anchor fastening system, and needle disposing system;
   d. wherein the driver arm and receiver are configured to be actuated to engage a gear system within the center assembly, thereby driving a suture unit through two edges of tissue until the fixed anchor abuts against the tissue, securing said edges of tissue by fastening a crimped anchor onto the distal end of the suture, disjoining the distal end of the suture from the needle; disposing of the needle.

2. A suturing device comprising:
   a. a driver arm and receiver arm connected by a hinge at the proximal ends of each arm, said hinge being configured to allow said distal ends of said driver arm and said receiver arm to converge and separate through rotation about said hinge while keeping said proximal ends of both arms affixed to each other;

b. a middle arm comprising a proximal end rotating about said hinge, a spring connecting said proximal end to the receiver arm; and a distal end connected in communication with the distal end of the driver arm via a biasing coil spring;

c. one or more suture units capable of securing wound tissue, said suture units comprising a length of a suture having a proximal end and a distal end and a fixed anchor joining the proximal and distal ends of the suture, forming a loop;

d. a suture-fastening mechanism, actuated by the compression of said biasing coil spring, said suture-fastening mechanism comprising a suture unit loading system, a crimped anchor loading system; and a crimped anchor fastening system;

e. a needle for catching said suture unit and piercing tissue, said needle comprising a proximal end affixed to the distal end of said receiver arm; and a distal end with a hook for catching said suture unit.

* * * * *